US009255139B2

(12) United States Patent
Huss et al.

(10) Patent No.: US 9,255,139 B2
(45) Date of Patent: Feb. 9, 2016

(54) TISSUE INHIBITOR OF METALLOPROTEINASES (TIMP) LINKED TO GLYCOSYLPHOSPHATIDYLINOSITOL (GPI)-ANCHORS FOR TREATMENT OF CANCER AND SKIN LESIONS

(75) Inventors: Ralf Huss, Waakirchen (DE); Peter J. Nelson, Munich (DE)

(73) Assignee: Peter Jon Nelson, Munich (DE)

( * ) Notice: Subject to any disclaimer, the term of this patent is extended or adjusted under 35 U.S.C. 154(b) by 1562 days.

(21) Appl. No.: 11/992,213

(22) PCT Filed: Sep. 20, 2006

(86) PCT No.: PCT/EP2006/009145

§ 371 (c)(1), (2), (4) Date: Jan. 18, 2011

(87) PCT Pub. No.: WO2007/039109

PCT Pub. Date: Apr. 12, 2007

(65) Prior Publication Data

US 2011/0105407 A1 May 5, 2011

(30) Foreign Application Priority Data

Sep. 20, 2005 (EP) .................................... 05020462

(51) Int. Cl.

| | |
|---|---|
| ***A61K 38/57*** | (2006.01) |
| ***C07K 14/81*** | (2006.01) |
| ***C07H 21/04*** | (2006.01) |
| ***C12N 15/63*** | (2006.01) |
| ***C12N 5/10*** | (2006.01) |
| ***A61P 35/00*** | (2006.01) |
| ***A61K 47/48*** | (2006.01) |

(52) U.S. Cl.

CPC ....... *C07K 14/8146* (2013.01); *A61K 47/48053* (2013.01); *A61K 47/48238* (2013.01)

(58) Field of Classification Search

None

See application file for complete search history.

(56) References Cited

U.S. PATENT DOCUMENTS

| | | | |
|---|---|---|---|
| 2002/0010162 A1* | 1/2002 | Fleischmajer | 514/152 |
| 2003/0157687 A1* | 8/2003 | Greene et al. | 435/226 |
| 2003/0176332 A1* | 9/2003 | Olmarker | 514/12 |

FOREIGN PATENT DOCUMENTS

WO WO-01/57068 8/2001

OTHER PUBLICATIONS

Djafarzadeh et al. Exogenously added GPI-anchored tissue inhibitor of matrix metalloproteinase-1 (TIMP-1) displays enhanced and novel biological activities, Jul. 2004, Biol. Chem., vol. 385, pp. 655-663.*

Djafarzadeh et al., Exogenously added GPI-anchored tissue inhibitor of matrix metalloproteinase-1 (TIMP-1) displays enhanced and novel biological activities, Biol. Chem., vol. 385, pp. 655-663, Jul. 2004.

Ahonen et al., Tissue inhibitor of metalloproteinases-3 induces apoptosis in melanoma cells by stabilization of death receptors, Oncogene (2003) 22, 2121-2134.

Nagel et al., Expression of matrix metalloproteinases MMP-2, MMP-9 and their tissue inhibitors TIMP-1, -2, and -3 in benign and malignant tumors of the salivary gland, Histopathology 2004, 44, 222-231.

Hayakawa et al., Growth-promoting activity of tissue inhibitor of metalloproteinases-1 (TIMP-1) for a wide range of cells, Federation of European Biochemical Societies, vol. 298, No. 1, 29-32.

Ikenaka et al., Tissue inhibitor of metalloproteinases-1 (TIMP-1) inhibits tumor growth and angiogenesis in the TIMP-1 transgenic mouse model, Int. J. Cancer: 105, 340-346 (2003).

Bond et al., Tissue Inhibitor of Metalloproteinase-3 Induces a Fas-associated Death Domain-dependent Type II Apoptotic Pathway, The Journal of Biological Chemistry, vol. 227, No. 16, Issue of Apr. 19, pp. 13787-13795, 2002.

Moniaux et al., Multiple roles of mucins in pancreatic cancer, a lethal and challenging malignancy, British Journal of Cancer, (2004) 91, 1633-1638.

Apostolopoulos et al., The immunogenecity of MUCI peptides and fusion protein, Elsevier, Cancer Letters 90 (1995) 21-26.

Jiang, Complex roles of tissue inhibitors of metalloproteinases in cancer, Oncogene (2002) 21, 2245-2252.

Djafarzadeh et al., GPI-anchored TIMP-1 treatment renders renal cell carcinoma sensitive to FAS-meditated killing, Oncogene (2005), 1-13.

Gillard et al., Matrix metalloproteinase activity and immunohistochemical profile of matrix metalloproteinase-2 and -9 and tissue inhibitor of metalloproteinase-1 during human dermal wound healing, Wound Repair and Regeneration, 12: 295-304 May-Jun. 2004.

Fujiwara et al., Keloid-derived fibroblasts show increased secretion of factors involved in collagen turnover and depend on matrix metalloproteinase for migration, British Journal of Dermatology 2005 153, pp. 295-300.

Razzaque et al., Expression profiles of collagens, HSP47, TGF-β1, MMPs and TIMPs in epidermolysis bullosa acquisita, Cytokine 21, (2003) 207-213.

(Continued)

*Primary Examiner* — James H Alstrum Acevedo
*Assistant Examiner* — Tara Martinez
(74) *Attorney, Agent, or Firm* — Wolf, Greenfield & Sacks, P.C.

(57) ABSTRACT

The present invention relates to fusion constructs of glycosylphosphatidylinositol (GPI)-anchored tissue inhibitors of metalloproteinases (TIMPs) and their use for the treatment of cancer and in regenerative medicine. By this approach, the GPI-anchored TIMP proteins are incorporated into the surface membrane of tumor cells and render tumor cells sensitive to FAS-induced apoptosis. Furthermore, the fusion constructs of the present invention are effective agents useful in wound healing applications. In one embodiment, the TIMP is linked to mucin followed by GPI in order to enhance surface presentation. The use of GPI to link TIMP renders the resulting fusion protein particularly useful as an anti-cancer agent for the treatment of cancer, and, in particular, any residual cancer following an incomplete surgical resection of primary tumors in an individual.

21 Claims, 22 Drawing Sheets

(56) References Cited

OTHER PUBLICATIONS

Ulrich et al., TIMP-1, MMP-2, MMP-9, and PIIINP as Serum Markers for Skin Fibrosis in Patients following Severe Burn Trauma, Plastic and Reconstructive Surgery, Apr. 1, 2003, pp. 1423-1431.

Written Opinion of the International Searching Authority Re: PCT/EP2006/009145, dated Mar. 26, 2008.

International Search Report Re: PCT/EP2006/009145 dated Mar. 2, 2007.

Ito et al., Mar. 18, 1996, revised form Apr. 29, 1996; Degradation of Interleukin 1β by Matrix Metalloproteinases; The Journal of Biological Chemistry, pp. 14657-14660.

Djafarzadeh et al., Apr. 27, 2012, Recombinant GPI-Anchored TIMP-1 Stimulates Growth and Migration of Peritoneal Mesothelial Cells, PLoS ONE, vol. 7, Issue 4.

Djafarzadeh et al., Oct. 25, 2012, Treatment of Dermal Fibroblasts with GPI-Anchored Human TIMP-1 Protein Moderates Processes Linked to Scar Formation, The Society for Investigative Dermatology, pp. 1-9.

* cited by examiner

C

D

A
Proliferation activity
0.5
0.4
0.3
0.2
0.1
0.0
24 h
48 h
72 h
FCS
Buffer
900
100
200
300
400
500
600
700
800
900
rhTIMP-1 [ng/ml]
TIMP-1-GPI [ng/ml]
B
Proliferation activity
0.5
0.4
0.3
0.2
0.1
0.0
24 h
48 h
72 h
FCS
Buffer
900
100
200
300
400
500
600
700
800
900
rhTIMP-1 [ng/ml]
TIMP-1-GPI [ng/ml]
C
Proliferation activity
0.5
0.4
0.3
0.2
0.1
0.0
24 h
48 h
72 h
FCS
Buffer
900
100
200
300
400
500
600
700
800
900
rhTIMP-1 [ng/ml]
TIMP-1-GPI [ng/ml]

TISSUE INHIBITOR OF METALLOPROTEINASES (TIMP) LINKED TO GLYCOSYLPHOSPHATIDYLINOSITOL (GPI)-ANCHORS FOR TREATMENT OF CANCER AND SKIN LESIONS

CROSS-REFERENCE TO RELATED APPLICATIONS

This application is the national phase under 35 U.S.C. section 371 of PCT International Application No. PCT/EP2006/009145, which has an International filing date of Sep. 20, 2006, which claims priority of European Patent Application 05020462.7, filed Sep. 20, 2005. The contents of each of these applications are incorporated herein by reference in their entirety.

FIELD OF THE INVENTION

The present invention relates to the field of fusion constructs and their use for the treatment of cancer and in regenerative medicine. Specifically, the invention relates to constructs comprising glycosylphosphatidylinositol (GPI)-anchored tissue inhibitors of metalloproteinases (TIMPs). Additionally, the fusion constructs of the present invention are effective regenerative agents useful in the field of wound healing applications.

BACKGROUND OF THE INVENTION

TIMPs in Cancer Research

The treatment of cancer remains a demanding task and employs different therapeutic approaches and strategies, offering varying degrees of success. One known approach is to increase the sensitivity of cancer cells to immune-mediated lysis. The sensitivity of tumors to immune-mediated lysis has been linked to the biology of matrix metalloproteinases (MMPs), and specifically, to the cell surface expression of MMPs by the tumor target cell. Matrix metalloproteinases (MMPs) degrade components of the extracellular matrix (ECM) and have been implicated in tissue remodeling, tumor invasion and metastasis (Egeblad & Werb, 2002; Itoh & Nagase, 2002). MMP activity has also been associated with the efficiency of both perforin/granzyme- and FAS-mediated apoptosis (reviewed in Egeblad & Werb, 2002). It was shown that MMP activity is regulated at many levels including four endogenous inhibitors, the tissue inhibitor of matrix metalloproteinases (TIMP-1, -2, -3 and 4 (Bode & Maskos, 2003). The in vivo balance between MMPs and TIMPs determines whether matrix resorption or deposition occurs (Nagase & Woessner, 1999).

The endogenous tissue inhibitors of metalloproteinases (TIMPs) exhibit diverse physiological/biological functions including the moderation of tumor growth, metastasis and apoptosis. These diverse biologic activities of TIMPs have been linked in part to the stochiometry of TIMP/MMP/cell surface protein interactions. The recruiting of cytotoxic lymphocytes represents one potential pathway in the defense against tumors. Although cytotoxic T lymphocytes (CTL) and natural killer (NK) cells that infiltrate and recognize tumor cells are identified, an effective anti-tumor immunity often fails to efficiently develop. This inefficacy is one reason that prevents the complete elimination of residual tumor cells after incomplete surgical resection, either due to an advanced stage of disease or local inoperability. The etiology of this functional deficiency in cytotoxic lymphocytes is currently unclear.

In general, the anti-tumor effects of CTLs and NK cells are mediated through either the perforin/granzyme or FAS-mediated (CD95/CSD95L) apoptotic pathways (Kagi et al., 1994). The perforin pathway is mediated by cytotoxins secreted during CTL or NK recognition of target cells (Kagi et al., 1994). The CD95, or FAS death receptor, belongs to the regulator of cell death family of proteins and is of central importance in immune mediated apoptosis of tumor cells (Nagata, 1999). Human FAS/CD95/Apo-1 is a single transmembrane glycoprotein receptor (325 amino acids, 45-48 kDa). The FAS ligand (FAS ligand, FASL, CD95L) is an integral membrane protein and is a type II transmembrane glycoprotein. FASL is a member of the TNF family, which includes TNF$\alpha$, $\alpha$- and $\beta$-chains of lymphotoxin (LT), CD40 ligand and CD30 ligand. The action of FAS is mediated via FADD (FAS-associated death domain)/MORT1, an adapter protein that has a death domain at its C-terminus and binds to the cytoplasmic death domain of FAS. Many tumors have been found to be resistant to apoptosis mediated through the FAS pathway (Frost et al., 2003; reviewed in Igney & Krammer, 2002).

As a model system to test the TIMP-GPI constructs of the present invention, cell lines of renal cell carcinoma have been used as an example. Renal cell carcinoma (RCC) is the seventh leading cause of cancer. Approximately one-third of patients with RCC have metastatic disease at presentation and up to 50% relapse following nephrectomy (Vogelzang & Stadler, 1998). RCC is difficult to treat and immunological therapies such as interferon-alpha and interleukin-2 are generally more effective than chemotherapy or radiation (Vogelzang & Stadler, 1998). Cytotoxic lymphocytes represent a potential component in the defense against tumors including RCC.

One member of the TIMP family, TIMP-1, is a broadly acting MMP inhibitor (Bode & Maskos, 2003). It is a soluble protein that can be detected on the cell surface only through its association with surface bound proteins (Brew et al., 2000; Klier et al., 2001). The overall role of TIMP-1 in cancer biology remains the subject of conflicting reports (Brand, 2002). To date, it is accepted that TIMP-1 plays a role in angiogenesis, cell migration, and proliferation (Brand, 2002). Recently, it was shown that a GPI-anchored TIMP-1 protein exhibited a pronounced suppression of endothelial cell migration in response to bFGF (Djafarzadeh R et al., 2004).

The conventional strategies and approaches for cancer therapy still suffer from the problem that tumor cells are difficult to eliminate once the tumor has developed. Primary tumors are usually removed from the patient by surgery. However, in some cases not all regions are available to the surgeon, and, thus, tumor cells remain in the body where they can develop into secondary tumors. This is a result of the incomplete surgical resection of the primary tumor.

The present invention therefore provides an effective anti-cancer agent and strategy in order to reduce or alleviate the proliferation of tumor cells in an individual, in particular in a patient that was subjected to an incomplete surgical resection of a primary tumor. The anti-cancer agents of the present invention are useful for killing tumor cells both in cell lines in vitro and in tissues in vivo.

The Role of TIMPs in Regenerative Medicine

The present invention is furthermore useful in the field of regenerative medicine. One significant area in the field of regenerative medicine is concerned with the wound healing process. Wound healing relates to a natural restorative response to tissue injury and involves a complex cascade of cellular events that ultimately generates the resurfacing, reconstitution, and restoration of the tensile strength of injured tissue. This process generally engages the recruitment and proliferation of different cell types, an elaboration of the cellular matrix, and an increase in immune surveillance.

Wound healing proceeds in a timely, sequential manner and can be divided into four general phases: inflammation, granulation, re-epithelialization and tissue remodeling. Each phase of the wound healing process is regulated by special signal transduction pathways. During wound healing, an increase in the expression of growth factors and cytokines occurs; in particular, increases in the levels of TNF, IL-1, and IL-6, have been described. During the initial inflammation phase, which involves the effector proteins IL-1, TNF-$\alpha$ and CSF, both macrophages and neutrophils are recruited to form a fibrin clot. During the granulation phase, the fibroblasts proliferate, migrate to the wound, and secrete ECM. The effector proteins involved in this latter phase include MMPs, PDGF, FGF, EGF and VEGF. The third phase in wound healing, re-epithelialization, is characterized by the proliferation of keratinocytes, which migrate into the wound, and also by an increase in myofibroblasts, which are responsible for wound contraction. The result of this phase, which involves the effector proteins MMPs, KGF, TGF, GM-CSF, EGF and uPA and tPA, is the re-epithelialization of the wound surface, the dissection of eschar, and the formation of a barrier. Finally, during the tissue remodeling phase, fibroblasts produce a collagenous matrix leading to the formation of scar tissue, apoptosis of fibroblasts, and a switch from the activation to differentiation of the keratinocytes. Known effector proteins involved in this last phase of wound healing include TGF-b1, MMPs and TIMPs.

Thus, the effector cells responsible for most aspects of wound healing are the fibroblasts and the keratinocytes, and MMPs that play an important role in both the migration of fibroblasts (MMP-1, -2, -3 and -13) and keratinocytes (MMP-1, -2, -3, and -10) (Singer & Clark, 1999) in addition to scar formation. Each of the MMPs has a different substrate specificity within the ECM, and play an important role in ECM degradation and turnover. The MMP family includes, inter alia, collagenases (MMP-1, MMP-8, MMP-13, MMP-18), stromelysins (MMP-3, MMP-10, MMP-11), gelatinases (MMP-2, MMP-9), matrilysin (MMP-7), metalloelastase (MMP-12) and a series of membrane-bound matrix metalloproteinases (MT-MMPs). As the function of MMPs is to proteolytically break down the surrounding ECM, a balance between this protease activity and ECM deposition during wound healing, i.e. re-building of the injured tissue, needs to be optimally maintained. The control of MMP activity is modulated by the TIMP proteins, which are produced by most cells, and act to inhibit the MMPs in a 1:1 ratio. Where this delicate balance between the proteolytic breakdown and deposition of ECM is disturbed, disorders such as abnormal wound healing may result, for example, chronic wounds, excessive scarring or keloid scarring.

Therefore, there exists a need to control or influence the physiological balance between protease activity and ECM deposition during the wound healing process.

In a further embodiment, the fusion constructs of the present invention provide an effective regenerative agent for the treatment of conditions defined by a disturbed balance between MMP protease activity and ECM deposition as, for example, in keloid scarring or chronic wounds, that are commonly associated with increased MMP levels. Additionally, the fusion constructs of the present invention provide an effective regenerative agent that can reduce, minimize or inhibit the formation of scars during the wound healing process.

SUMMARY OF THE INVENTION

The present invention provides novel anti-tumor agents and methods for the treatment of cancer.

The present invention is based on the surprising finding that GPI-anchored TIMP effectively reduces or alleviates cancer cell proliferation, and promotes the killing of cancer cells in cell lines both in vitro and in vivo. The structural and functional determinants of TIMP have been combined with a glycosylphosphatidylinositol (GPI) anchor, and, optionally, with mucin, in order to generate a highly effective chemotherapy agent. This approach exploits TIMP proteins anchored by glycosylphosphatidylinositol (GPI) to be incorporated into surface membranes when purified and added to cancer cells. The fusion of TIMP-GPI with a mucin domain further enhances the presentation of TIMP proteins on the surface cell membrane and makes the fusion construct more effective in rendering the cancer cells sensitive to immune-mediated destruction.

In the following examples, the present invention demonstrates that TIMP has the potential for the inhibition of growth of tumor cells and reduction of tumor development both in cell lines in vitro and in tissues in vivo. The linking of TIMP to a GPI-anchor and exogenous administration of GPI-anchored TIMP results in an efficient insertion of TIMP protein into the cell membranes of cancer cells. The GPI-anchored TIMP-1 surface expression induced a variety of biological effects in cancer cell lines with potential therapeutic relevance such as inducing the FAS-mediated apoptotic pathway in cancer cells. As shown in the following examples, the suppression of cancer cell proliferation was observed to be dose-dependent.

GPI-anchored TIMP-1 protein also blocked secretion of proMMP-2 and proMMP-9 and dramatically altered the cell surface association of diverse MMPs. Most significantly, the normally FAS-apoptosis resistant tumor cell lines were rendered sensitive to FAS/CD95-mediated killing. GPI-TIMP treatment results in a down regulation of anti-apoptotic BCL2 protein and a corresponding increase in pro-apoptotic BAX protein. This shift towards a higher concentration of pro-apoptotic proteins may be one reason for the increased sensitivity of FAS-mediated apoptosis of TIMP surface engineered cancer cells.

Using the above approach, the GPI-anchored TIMP proteins or polypeptides of the present invention have been proved to be particularly useful in therapeutic applications in the treatment of residual cancer after incomplete surgical resection of the primary tumor like in advanced breast cancer, osteosarcoma, renal cell carcinoma or in malignant brain tumors, e.g. glioblastoma.

Moreover, since tumor cells, including renal cell carcinoma (RCC), are intrinsically resistant to FAS-mediated killing, the present invention provides an effective means to render the tumor cells susceptible to FAS-mediated apoptosis.

In a first aspect, the present invention therefore relates to a fusion construct (TIMP-GPI or TIMP-mucin-GPI) comprising an amino acid sequence of a tissue inhibitor of metalloproteinases (TIMP) or a biologically active fragment thereof, wherein said TIMP or biologically active fragment thereof is linked to an amino acid sequence of a mucin domain followed by an amino acid sequence of a glycosylphosphatidylinositol (GPI)-anchor.

In a preferred embodiment, the 3'-end of TIMP is fused directly to a GPI-linking sequence and does not contain a mucin domain.

The term "mucin" relates to a family of large, heavily glycosylated proteins. One class of mucins are membrane-bound due to the presence of a hydrophobic membrane-spanning domain that favors retention in the plasma membrane, while another class of mucins are secreted on mucosal surfaces. Mucin genes encode mucin monomers that are typically synthesized as rod-shape apomucin cores that are post-translationally modified by exceptionally abundant glycosylation. Two distinctly different regions are found in mature mucins. One region includes the amino- and carboxy-terminal regions, which are lightly glycosylated, but rich in cysteine residues, which are likely involved in establishing disulfide linkages within and among mucin monomers. The second central region is formed of multiple tandem repeats of 10 to 80 residue sequences, wherein over half of the amino acid residues are serine or threonine.

Mucins are generally secreted as massive aggregates of proteins having molecular masses of roughly 1 to 10 million Daltons. Within these aggregates, monomers are linked to one another mostly by non-covalent interactions, although intermolecular disulfide bonds may also play a role in this process. At least 19 human mucin genes have been distinguished including MUC1, 2, 3A, 3B, 4, 5AC, 5B, 6-9, 11-13, and 15-19.

The mucin as used in the present invention is preferably a membrane-bound mucin domain and comprises preferably an amino acid sequence selected from the group consisting of MUC1, MUC3A, MUC3B, MUC4, MUC11, MUC12, MUC16, and MUC17, or a variant or portion thereof (the above mucins are reviewed in Moniaux N et al., 2004). In another preferred embodiment, a mucin-stalk is used that is isolated from the surface-associated chemokine CXCL16 or fractalkine (CX3CL1).

Fractalkine is a member of the large and complex chemokine gene superfamily, which consists principally of secreted, proinflammatory molecules. The typical core structure of chemokines is partially maintained by disulfide bonds between positionally conserved cysteine resides. For most of chemokine peptides, a familiar structural characteristic is the distribution of four cysteines within the molecule, i.e. a cysteine signature motif: CXC, CC and C, where C is a cysteine and X is any amino-acid residue. Four different chemokine families have been identified based on the observation that chemokine peptides can be distinguished by the organization of the cysteine residues located near the N-terminus of the molecule. Fractalkine itself defines one of the chemokine families, and is distinguished structurally from other chemokine families as the N-terminal cysteines of fractalkine are separated by three residues (i.e. a CX3C motif) as well as being tethered to the cell membrane by an extended C-terminus transmembrane anchor that includes a mucin-like domain, or a mucin-like stalk. Thus, the mucin and fractalkine domains contained within the fusion constructs of the present invention are suitable for achieving an improved anchoring of the TIMP protein in the cell membrane.

The TIMP as used in the present is preferably derived from a mammal; more preferred is a human (the four TIMPs are reviewed in Mannello F et al., 2001). Examples of TIMP proteins that can be used in accordance with the present invention comprise TIMP-1, TIMP-2, TIMP-3, or TIMP-4 and their corresponding variants in other organisms such as mouse, rabbit, dog, cat, sheep, and cow.

The GPI-anchor as used in the present invention is preferably derived from the lymphocyte function-associated antigen (LFA-3), or a portion thereof, and includes a GPI-signal sequence that mediates membrane association.

The present invention also relates to a nucleic acid molecule, such as RNA or DNA, comprising a nucleic acid sequence that encodes for the GPI-anchored TIMP construct of the invention.

In a further aspect of the present invention, the nucleic acid molecule of the invention is contained in an expression plasmid, a vector or a host cell for expression of the nucleic acid molecule of the invention.

The present invention also relates to the use of the TIMP-GPI- or TIMP-mucin-GPI fusion constructs of the invention for the treatment of cancer, particularly residual cancer after surgical removal of a primary tumor.

In a further aspect of the present invention, the TIMP-GPI or TIMP-mucin-GPI fusion constructs of the invention are contained in a pharmaceutical composition or medicament. In a further embodiment, the TIMP-GPI or TIMP-mucin-GPI fusion constructs of the invention are suitably used as anti-cancer agents or drugs. In a preferred embodiment, the anti-cancer drugs of the invention are administered and applied locally to the side of the tumor mass resection in high-risk tumor patients with a high risk of residual cancer cells and increased incidence of a local relapse, and in those patients having an obvious residual tumor due to advanced stage disease or local inoperability. Preferably, the fusion construct is administered by spraying into the wound and/or injection into regions that are not available for surgery.

The present invention also relates to an in-vitro method for inhibition of cancer cell proliferation comprising the steps of subjecting a cancer cell line to an effective amount of TIMP-mucin-GPI or TIMP-GPI fusion construct.

In a further embodiment, the present invention provides novel agents and methods for the treatment of conditions defined by a disturbed balance between normal physiological MMP protease activity and ECM deposition, which result in abnormal wound healing. In one embodiment, the present invention provides agents and methods suitable for the treatment of keloid or hypertrophic scarring and chronic wounds commonly associated with increased MMP levels. Furthermore, the present invention also provides effective agents and methods for reducing, minimizing or inhibiting the formation of scars during the wound healing process.

DEFINITIONS

With the term "TIMP" as used herein is meant an endogenous tissue inhibitor of metalloproteinases, which is known to be involved in physiological/biological functions including the inhibition of active matrix metalloproteinases, regulation of pro MMP activation, cell growth, and the modulation of angiogenesis. The human "TIMP family" contains four members, TIMP-1, TIMP-2, TIMP-3, and TIMP-4. One preferred member used in the present invention, TIMP-1, is a secreted protein that can be detected on the cell surface through its interaction with surface proteins (Bode & Maskos, 2003).

The term "fusion construct" or "TIMP fusion construct" as used herein refer to both the nucleic acid molecule and the amino acid molecule encoded thereby.

The invention specifically relates to nucleic acids containing a nucleotide sequence including the sequence defined by SEQ ID NOS:1-5, or a homolog thereof, or unique fragments thereof. In the present invention, the sequence of a nucleic acid molecule that encodes the resulting protein is considered homologous to a second nucleic acid molecule if the nucleotide sequence of the first nucleic acid molecule is at least about 70% homologous, preferably at least about 80% homologous, and more preferably at least about 90% homologous to the sequence of the second nucleic acid molecule. Homology between two nucleic acid sequences may be readily determined using the known BLASTN algorithm (Altschul, et al., 1990) with default settings. As a further example, another known test for ascertaining the homology of two nucleic acid sequences is whether they hybridize under normal hybridization conditions, preferably under stringent hybridization conditions.

Given the nucleic acid sequence disclosed herein, the skilled person can readily design nucleic acid structures having particular functions in various types of applications. For example, the artisan can construct oligonucleotides or polynucleotides for use as primers in nucleic acid amplification procedures, such as the polymerase chain reaction (PCR), ligase chain reaction (LCR), Repair Chain Reaction (RCR), PCR oligonucleotide ligation assay (PCR-OLA), and the like. Oligonucleotides useful as probes in hybridization studies, such as in situ hybridization, can be constructed. Numerous methods for labeling such probes with radioisotopes, fluorescent tags, enzymes, and binding moieties (e.g., biotin) are known, thus the probes of the invention can be readily adapted for easy detectability.

Oligonucleotides can also be designed and manufactured for other purposes. For example, the invention enables the design of antisense oligonucleotides, and triplex-forming oligonucleotides for use in the study of structure/function relationships. Homologous recombination can be implemented by adaptation of the presently described nucleic acid for use as a targeting means.

The protein encoded by the nucleic acid of the present invention further includes functional homologs. A protein is considered a functional homolog of another protein for a specific function, as described below, if the homolog has the same function as the other protein. The homolog can be, for example, a fragment of the protein, or a substitution, addition, or deletion mutant of the protein.

Determination of whether two amino acid sequences are substantially homologous is, for the purpose of the present invention, based on FASTA searches according to Pearson & Lipman (1988). For example, the amino acid sequence of a first protein is considered homologous to that of a second protein if the amino acid sequence of the first protein has at least about 70% amino acid sequence identity, preferably at least about 80% identity, and more preferably at least about 95% identity, with the sequence of the second protein.

The possibility of substituting one amino acid in a sequence with an equivalent amino acid is well-known. Groups of amino acids known to be equivalent include:

(a) Ala(A), Ser(S), Thr(T), Pro(P), Gly(G);

(b) Asn(N), Asp(D), Glu(E), Gln(Q);

(c) His(H), Arg(R), Lys(K);

(d) Met(M), Leu(L), Ile(I), Val(V); and (e) Phe(F), Tyr(Y), Trp(W).

Substitutions, additions, and/or deletions in the amino acid sequences can be made as long as the protein encoded by the nucleic acid of the invention continues to satisfy the functional criteria described herein. An amino acid sequence that is substantially the same as another sequence, but that differs from the other sequence by means of one or more substitutions, additions, and/or deletions, is considered to be an equivalent sequence.

Preferably, less than 20%, more preferably less than 10%, and still more preferably less than 5%, of the number of amino acid residues in a sequence are substituted for, added to, or deleted from the protein encoded by the nucleic acid of the invention.

With the term "MMP" as used herein is meant a matrix metalloproteinase that belongs to the MMP superfamily as represented by at least 26 extracellular matrix-degrading metalloendopeptidases that are acting during tissue development and differentiation, cellular infiltration, wound healing, and as moderators of the immune response.

With the term "GPI" as used herein is meant glycoinositol phospholipids, in particular, glycosylphosphatidlyinositol as described in Medof et al., 1996. These phospholipid-like anchors have a common structure for membrane attachment irrespective of protein function. GPI anchoring units are composed of a linear glycan containing a phosphoethanolamine, three mannose residues, and a non-acetylated glucosamine linked to an inositol phospholipid. The GPI sequence contains the signals that direct GPI anchoring.

With the term "mucin" or "mucin domain" as used herein is meant a membrane bound or non-membrane glycoprotein component. Usually, membrane-bound mucins exhibit hydrophobic sequences or transmembrane domains responsible for their anchoring in the lipid bilayer and, optionally, contain one or several von Willebrandt factor-like domains, which function in the oligomerization of mucin monomers and in the packaging into secretory vesicles. The term "mucin" or "mucin domain" as used herein also encompasses mucin-stalks or mucin-like domains, such as the mucin-stalks typically found in the CXCL16 chemokines or in fractalkine (CX3CL1).

A "TIMP-GPI" fusion construct as used herein relates to TIMP that is fused directly to a GPI-linkage sequence. The TIMP-GPI fusion construct is designed by substituting the 3'-mRNA or cDNA end sequence of naturally GPI-anchored proteins (i.e., a sequence that contains the signals that direct GPI anchoring) for the endogenous TIMP 3'-mRNA or cDNA end sequence.

A "TIMP-mucin-GPI" or "TIMP-muc-GPI" as used herein relates to a TIMP that is directly fused to a mucin domain followed by a GPI-linking sequence. The TIMP-mucin-GPI fusion construct is designed as described for TIMP-GPI but including the amino acid sequence of a mucin domain between the amino acid sequences of TIMP and GPI. By analogy, "TIMP-fractalkine-GPI" or "TIMP-frac-GPI" relates to a TIMP that is directly fused to a fractalkine domain followed by a GPI-linking sequence.

With the term "RCC" is meant renal cancer carcinoma which is considered to be a progressive tumor with limited therapeutic options due to tumor resistance to current chemotherapeutic agents and radiation. RCC serves as a model system in the present invention to show the anti-tumor activity of GPI-anchored TIMP. The model cell lines used in the present invention are the RCC-26 and RCC-53 cell lines that were established from patients with stage I and stage IV cell carcinomas.

With the term "FAS" is meant a member of the tumor necrosis factor/nerve growth factor receptor family that induces apoptosis independent of TNF-$\alpha$. Other abbreviations known in the art for FAS are Apo1 (=Apoptosis inducing protein 1) and CD95.

The term "regeneration" generally refers to restoring the integrity of traumatized or otherwise injured tissue. This term can include the processes of wound healing, tissue repair, and other types of restorative activities occurring at the location where a physiological insult and ensuing tissue damage has occurred.

DETAILED DESCRIPTION OF THE INVENTION

The TIMP Family and Protein Engineering of Cellular Surfaces

Tissue inhibitors of metalloproteinases (TIMPs) are known as the major cellular inhibitors of the matrix metalloproteinase (MMP) sub-family, exhibiting varying degrees of efficacy against different MMP members, as well as different tissue expression patterns and modes of regulation. The TIMPs typically modulate the activity of soluble, matrix bound and cell associated MMPs. All four mammalian TIMPs have many broad similarities, but exhibit distinctive structural features, biochemical properties and expression patterns, which suggests that each TIMP has a particular in vivo function.

The TIMP-1 protein is the most widely expressed and studied member of the TIMP family. Other members of the TIMP family include TIMP-2, TIMP-3 and TIMP-4. TIMP proteins not only share common structural features, including a series of conserved cysteine residues that form disulfide bonds essential for the native protein conformation (Brew et al., 2000), but they also have widely overlapping biological activities. The conserved N-terminal region of the TIMP proteins is necessary for functional inhibitory activities, while the divergent C-terminal regions are thought to modulate the selectivity of inhibition and binding efficiency of agents to the MMPs (Maskos & Bode, 2003). However, apart from their ability to act as MMP inhibitors, the various TIMP family members may also exhibit additional biological activities, including the regulation of proliferation and apoptosis in addition to the modulation of angiogenic and inflammatory responses.

TIMP-1 has been found to inhibit most MMPs (except MMP-2 and -14), and preferentially inhibits MMP-8. TIMP-1 is produced and secreted in soluble form by a variety of cell types and is widely distributed throughout the body. It is an extensively glycosylated protein with a molecular mass of 28.5 kDa. TIMP-1 inhibits the active forms of MMPs, and complexes with the proform of MMP9. Like MMP9, TIMP-1 expression is sensitive to many factors. Increased synthesis of TIMP-1 is caused by a wide variety of reagents that include: TGF beta, EGF, PDGF, FGFb, PMA, alltransretinoic acid (RA), IL1 and IL11.

TIMP-2 is a 21 kDa glycoprotein that is expressed by a variety of cell types. It forms a non-covalent, stoichiometric complex with both latent and active MMPs. TIMP-2 shows a preference for inhibition of MMP-2.

TIMP-3 is typically bound to the ECM and inhibits the activity of MMP-1, -2, -3, -9, and 13. TIMP-3 shows 30% amino acid homology with TIMP-1 and 38% homology with TIMP-2. TIMP-3 has been shown to promote the detachment of transformed cells from ECM and to accelerate morphological changes associated with cell transformation.

Due to its high-affinity binding to the ECM, TIMP-3 is unique among the TIMPs. TIMP-3 has been shown to promote the detachment of transformed cells from the ECM and to accelerate the morphological changes associated with cell transformation. TIMP-3 contains a glucosaminoglycan (GAG) binding domain comprising six amino acids (Lys30, Lys26, Lys22, Lys42, Arg20, Lys45) that are thought to be responsible for an association with the cell surface. TIMP-3 is the only TIMP that normally inhibits TACE (TNF-α-converting enzyme), another metalloprotease that releases soluble TNF and is responsible for the processing of the IL-6 receptor to thus play a central part in the wound healing process.

TIMP-4 inhibits all known MMPs, and preferentially inhibits MMP-2 and -7. TIMP4 shows 37% amino acid identity with TIMP1 and 51% homology with TIMP2 and TIMP3. TIMP4 is secreted extracellularly, predominantly in heart and brain tissue and appears to function in a tissue specific fashion with respect to extracellular matrix (ECM) homeostasis.

Protein engineering of cell surfaces is a potentially powerful technology through which the surface protein composition of cells can be manipulated without gene transfer. By substituting the mRNA derived cDNA sequence from a GPI-linked protein that contains the GPI signal domain for the carboxyl terminal region of a protein of interest, it is possible to generate a fusion construct that encodes a GPI-linked protein.

This approach offers multiple advantages over more traditional gene transfer approaches. For example, the method is applicable to cells that are difficult or impossible to transfect (e.g. primary microvascular endothelium, primary target cells, etc). The amount of protein added to the cell surface can be controlled and quantitated (by FACS or immunofluorescence). In addition, multiple GPI-anchored proteins can be sequentially or concurrently inserted into the same cells. Through molecular engineering it is possible to express an additional epitope tag that assists in protein purification as well as monitoring of reagent during experiments. The agent can be injected directly into the tumor or peritumorial area and the effect of selective leukocyte recruitment on tumor growth or FAS-induced apoptosis determined.

TIMP Fusion Constructs for the Treatment of Cancer

The prognosis of malignant tumors is mostly dependent on their clinical and pathological stage. While most carcinomas (e.g. primary and secondary tumors) can be completely surgically removed in most instances, the re-resection of advanced stage cancer is often not possible and associated with early recurrence of the disease and an increased disease-related mortality.

Particularly in breast cancer, advanced stage disease with extended tumor size (>2 cm) is associated with the occurrence of distant metastasis and limited survival. A large tumor volume is also considered to be a critical parameter for the presence of residual cancer, which presents also a high risk for local relapse and the propagation of distant metastasis. Likewise, brain tumors such as the glioblastoma (astrocytoma grade IV) is another conceivable target for the tumor surveillance, because complete surgical removal is almost always impossible and local relapse occurs in 95% of all cases within one year of primary surgery.

In order to solve the problem that is linked to residual cancer, it was necessary to identify a novel cancer therapy option that is particularly useful for the treatment of residual cancer after incomplete surgical resection.

As a solution, the present invention provides GPI-anchored TIMP, which can be applied locally into the resection margins to attract immune cells and focus the residual tumor surveillance on the residual cancer cells.

For this purpose, TIMP proteins are anchored by GPIs, and, when purified and added to cancer cells incorporate into their surface membranes and are fully functional. By substituting 3'-mRNA end sequences of naturally GPI-anchored proteins (i.e., a sequence that contains the signals that direct GPI anchoring) for the endogenous 3'-mRNA end sequence, virtually any TIMP protein can be expressed as a GPI-anchored derivative.

In the present invention, the incorporation of purified GPI-TIMP protein into the surface membranes of tumor cell lines is demonstrated by incubation of the cell lines with purified TIMP-1-GPI, TIMP-1-mucin-GPI or recombinant human (rh)TIMP-1 control protein. As detailed below, surface expression with GPI-anchored TIMP-1 resulted in a strong surface signal for TIMP-1.

As used herein, the terms "isolated and/or purified" refer to the in vitro isolation of a DNA or polypeptide molecule from its natural cellular environment, and from association with other components of the cell, such as nucleic acid or polypeptides, so that it can be sequenced, replicated, and/or expressed. For example, "isolated GPI linking sequence" is RNA or DNA containing greater than 9, preferably 36, and more preferably 45 or more, sequential nucleotide bases that encode at least a portion of a linking sequence, or a variant thereof, or a RNA or DNA complementary thereto, that is complementary or hybridizes, respectively, to RNA or DNA encoding the linking sequence and remains stably bound under stringent conditions, as defined by methods well known in the art. Thus, the RNA or DNA is "isolated" in that it is free from at least one contaminating nucleic acid with which it is normally associated in the natural source of the RNA or DNA and is preferably substantially free of any other mammalian RNA or DNA.

As used herein, the term "recombinant nucleic acid" e.g., "recombinant DNA sequence" refers to a nucleic acid, e.g., to DNA, that has been derived or isolated from any appropriate tissue source, that may be subsequently chemically altered in vitro, so that its sequence is not naturally occurring, or corresponds to naturally occurring sequences that are not positioned as they would be positioned in a genome which has not been transformed with exogenous DNA. An example of DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the known methodology of genetic engineering.

Unlike conventional polypeptide anchors, which have different transmembrane sequences and connect to specific cytoplasmic extensions, these phospholipid-like anchors use a common structure as a general mechanism for membrane attachment irrespective of protein function. GPI anchoring units are composed of a linear glycan containing a phosphoethanolamine, three mannose residues, and a non-acetylated glucosamine linked to an inositol phospholipid. They are prefabricated in the endoplasmic reticulum (ER) and are added to primary translation products at the time of their translocation across the ER membrane. The GPI-modified products then are glycosylated in the ER and Golgi, and subsequently transported to the cell surface.

Preferred GPI-linking sequences that can be used in the present invention are derived from GPI-anchors that are isolated from, for example, enzymes such as alkaline phosphatase, acetylcholinesterase, 5' nucleotidase (CO73); adhesion molecules such as lymphocyte function-associated antigen (LFA-3; CD58), neural cell adhesion molecule (NCAM); complement regulatory proteins such as decay accelerating factor (DAF or CD55), or others such as the Fey receptor type III B (Fc-y-RIII or CD16b), Thy-1 (CD90), Qa-2, Ly-6A, Membrane inhibitor of reactive lysis (MIRL or CD59). For the purpose of the present invention, the lymphocyte function-associated antigen (LFA-3) is preferred. The skilled person will recognize that also any other of the known GPI-anchors can be used for the practice of the present invention.

For the construction of TIMP-GPI, either the full-length sequence of TIMP can be used in the fusion construct or a functionally active portion thereof, which retains the activity of TIMP. Likewise also a portion of the GPI sequence can be used as long as the portion allows for the incorporation of the TIMP protein into the surface cell membrane of cancer cells.

In the following, a plurality of embodiments relating to the TIMP fusion constructs are described, whereby the constructs were produced and provided for treatment of cancer and as agents in the field of regenerative medicine. In a first embodiment, the TIMP molecule is selected from the group consisting of TIMP-1, TIMP-2, TIMP-3 and TIMP-4, and is preferably fused to a GPI sequence.

In another preferred embodiment, the GPI sequence is 36 amino acids in length.

In yet another embodiment, the TIMP molecule is selected from the group consisting of TIMP-1, TIMP-2, TIMP-3 and TIMP-4, and is fused to a mucin domain or fractalkine domain followed by the GPI sequence.

In a further embodiment, the TIMP protein that is selected from the group consisting of TIMP-1, TIMP-2, TIMP-3 and TIMP-4 and fused to the GPI sequence, or fused to a mucin domain or fractalkine domain followed by the GPI sequence, is truncated at the C-terminal. In a preferred embodiment, said TIMP molecule is truncated to the first 50, 50-100 or 50-152 N-terminal amino acid residues. More preferably, the TIMP molecule is truncated to the first 152 N-terminal amino acid residues and is the TIMP-1 molecule. The term "truncated" refers to a TIMP nucleic acid or amino acid sequence that contains less that the full number of nucleic acid bases or amino acid residues found in a native TIMP nucleic acid sequence or protein or to a nucleic acid or amino acid sequence has been deleted of non-desired sequences.

In yet a further embodiment, the TIMP fusion construct is defined by a sequence selected from the group consisting of SEQ ID NOs: 1, 2, 3, 4 and 5.

The obtained construct can then be expressed in any suitable cell line or host cell to obtain the functional TIMP polypeptide or protein. For this purpose, any of the suitable known vectors or plasmids can be used to express the GPI-anchored TIMP proteins of the present invention. As described in more detail below, target cancer cells treated with TIMP-GPI protein (and as control with rhTIMP-1 protein) were recognized by the protein constructs and, as consequence, killed due to FAS-mediated apoptosis.

In a preferred embodiment, and by way of example, one vector used for expression of the fusion constructs of the present invention contains the promoter for human elongation factor 1 alpha followed by a multiple cloning site and an internal ribosomal binding site which allows bicistronic expression of the construct and dihydrofolate reductase (DHFR) used as a selection marker (Mack, et al., P.N.A.S. USA 92:7021, 1995). The 3' end (carboxyl terminal) of the TIMP protein is fused either directly to a GPI-linkage sequence (e.g. derived from lymphocyte function-associated antigen-3 (LFA-3)) or the mucin-like domain isolated from CXCL16 or fractalkine (CX3CL1) followed by the GPI signal. As indicated above, these mucin regions are largely composed of serine/threonine/glycine/proline residues shown to facilitate cell-cell interactions. The resultant fusion constructs are transfected into dihydrofolate reductase (DHFR)-deficient Chinese hamster ovary (CHO) cells and the selection is performed as described (Mack, et al., P.N.A.S. USA 92:7021-7025, 1995). In a preferred embodiment, the transfectants can be exposed to methotrexate to increase the expression rate by gene amplification.

In a further embodiment, the TIMP-GPI construct can further be fused to a mucin domain to increase the efficiency of membrane incorporation of TIMP-GPI proteins. Mucins are membrane-bound or non-membrane glycoprotein components that were first identified in secreted mucus lining the surfaces of glandular epithelia. Membrane-bound mucins exhibit hydrophobic sequences or transmembrane domains responsible for their anchoring in the lipid bilayer. At present, a total of 21 genes have received the appellation MUC: MUC1-2, MUC3A, MUC3B, MUC4, MUC5AC, MUC5B, MUC6-13, MUC15-20 (Moniaux N, et al., 2004). The five common features of a mucin are: (1) secretion into the mucus layer, (2) high molecular weight O-glycoprotein, (3) presence of a tandem repeat array encoded by a unique and centrally positioned large exon, (4) presence of a predicted peptide domain containing a high percentage of serine and threonine residues, and (5) a complex pattern of mRNA expression. With one exception (MUC7), the secretory mucins (MUC2, MUC5AC, MUC5B and MUC6) possess one or several von Willebrandt factor-like domains, cysteine-rich peptides, which function in the oligomerization of mucin monomers and in the packaging into secretory vesicles. Typically, secreted mucins are expressed exclusively by specialized epithelial cells, are secreted in the mucus, and display a restricted expression pattern within the human body. The four secretory mucins, also referred to as the gel-forming mucins, have a common architecture with a high level of similarity to the pro-von Willebrand factor. They are also known to harbor five D domains because of their homology to the D domains of the von Willebrand factor.

The membrane-bound mucins are composed of MUC1, MUC3A, MUC3B, MUC4, MUC11, MUC12, MUC16, and MUC17. Membrane-anchored mucins contain a SEA (Sea urchin sperm protein, Enterokinase and Agrin) module, with the exception of MUC4. MUC3A-B, MUC4, MUC11-12, and MUC17 contain two to three epidermal growth factor (EGF)-like domains. Examples of membrane-bound mucins that can be used in the present invention are MUC1, MUC3, MUC4, and MUC12. In a preferred embodiment of the invention, the mucin-stalk of the surface-associated chemokine CXCL16 or fractalkine (CX3CL1) is used. CXCL16 is a member of the CXC chemokine subfamily. Unlike other members of this subgroup, CXCL16 is structurally different and has four distinct domains: a chemokine domain tethered to the cell surface via a mucin-like stalk, which in turn is attached to transmembrane and cytoplasmic domains. Fractalkine (CX3CL1) has a similar structure to that of CXCL16, and both CXCL16 and fractalkine act as adhesion molecules when expressed on cell surface, and upon cleavage from cell surface, the soluble chemokines act as chemoattractants.

Preferably, the mucin domain is fused between the 3'-end of the TIMP sequence and the 5'end of the GPI anchor sequence by any of the known conventional genetic engineering methods. The obtained TIMP-mucin-GPI fusion construct of the invention can then be transfected and expressed in any suitable known cell line or host cell. The skilled person will recognize that any other mucins or mucin domains are suitable for the purpose of the present invention.

In a preferred embodiment, the fractalkine fused to the TIMP molecule comprises amino acids 100-342 of CX3CL1 followed by the GPI sequence. In an even more preferred embodiment, the TIMP molecule is the TIMP-1 molecule truncated to the first 152 N-terminal amino acids (SEQ ID NO: 5).

Although the use of TIMP-1 (Bode & Maskos, 2003) for the preparation of GPI-anchored TIMP protein is preferred in the present invention, the skilled person will recognize that also other TIMP proteins may be used for the practice of the present invention. Further examples of human TIMPs that are useful are TIMP-2, TIMP-3, and TIMP-4 (Mannello F, et al., 2001). The used TIMPs are derived from human sources and administered to treat human cancer cells. The skilled person will likewise recognize that also homologs of TIMP, in particular TIMP-1, in other organisms than human will have a similar effect in killing tumor cells. For example, in some embodiments, the sequence of TIMP-1 derived from an animal such as dog, cat, mouse, rabbit, cow or sheep, and bird may be used for the construction of a TIMP-GPI fusion construct of the present invention. The TIMP-GPI chimera will subsequently be applied to the site of tumor in similar fashion as described for a human individual.

Tumors and cancer cells that may be treated with the GPI-anchored TIMP include the following but not limiting cancers: breast cancer, renal cancer, prostate cancer, leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, gastrointestinal cancer, lymph node cancer, esophagus cancer, colorectal cancer, pancreas cancer, ear, nose and throat (ENT) cancer, cancer of the uterus, ovarian cancer and lung cancer and the metastases thereof.

For treatment of residual cancer, TIMP-GPI can be administered and applied locally to the side of the tumor mass resection in high-risk tumor patients with a high risk of residual cancer cells and increased incidence of a local relapse and in those patients with an obvious residual tumor due to advanced stage disease or local inoperability. Preferably, the fusion construct is administered at a concentration of 0.5 to 5 μg/ml protein, more preferred at 0.5 to 1 μg, or 1 to 2 μg/ml. A concentration of about 1 μg/ml TIMP-GPI or TIMP-mucin-GPI is most preferred. The protein can be administered to the individual by any applicable administration routes. It is preferred that the treatment is carried out during surgery such that the fusion construct is sprayed into the wound or is injected into regions that are not available for surgery. For this purpose, the GPI-anchored TIMP fusion construct of the present invention can be a constituent of a pharmaceutical composition or medicament which further comprises one or more of the conventionally known carriers, diluents and excipients.

As concluded from the examples below, GPI-anchored TIMP appears to induce its anti-tumor activity, i.e. the killing of tumor cells, not by CTL- and NK cell-induced apoptosis (perforin/granzyme-mediated lytic pathway) but rather by the second pathway, which involves FAS/CD95-mediated apoptosis (for further details see examples 5 and 6; FIGS. 5 and 6). Furthermore, while many tumor cells are resistant to FAS-mediated apoptosis, treatment with TIMP-1-GPI, but not control rhTIMP-1, rendered the cell lines sensitive to FAS-mediated apoptosis.

It was also found that TIMP-1-GPI protein treatment reduces BCL2 and increases BAX protein expression. The BCL2 proteins represent a family of proteins involved in the control of apoptosis. Some members of this family (such as BCL2 and BCL-XL) are anti-apoptotic, while others (such as Bad or BAX) are pro-apoptotic. The sensitivity of cells to apoptotic stimuli depends on the balance between pro- and anti-apoptotic BCL2 family members. In addition, the effect of TIMP-1-GPI treatment on the expression of BCL2 and BAX was determined and it is shown that treatment of cancer cells with TIMP-1-GPI increased expression of pro-apoptotic BAX, and decreased expression of anti-apoptotic BCL2.

Similar results were obtained for the TIMP fusion constructs encoded by SEQ ID NOs:1, 2, 3, 4 and 5, respectively.

In summary, the availability of the methodology to produce microgram to milligram quantities of recombinant GPI-anchored TIMP proteins in conjunction with the incorporability of these molecules into surfaces of cancer cells provides an effective tool for the treatment of cancer.

The TIMP Fusion Constructs for Use in Regenerative Medicine

Furthermore, the fusion constructs of the present invention are suitable for use in regenerative medicine, particularly in the area of wound healing. As described above, TIMP proteins that are fused to GPI or to mucin-GPI or fractalkine-GPI are efficiently incorporated into the cellular surface membrane, where they focus functional domains on those cell surfaces independently of protein-protein interactions. The TIMP fusion constructs of the present invention are typically quite stable and display amplified and novel bioactivities.

As described above, both MMPs and TACE play a crucial role in the process of wound healing. Increased MMP levels are associated with various wound healing disorders, inter alia chronic wound occurrence. Because the TIMPs are natural inhibitors of MMPs, the fusion constructs of the present invention can also be employed as effective therapeutic agents for controlling the process of wound healing, for example, in regenerative medicine and are suitable for treating disorders characterized by an increase in MMP levels.

Thus, the present invention provides agents and methods suitable for use in regenerative medicine and/or to treat disorders characterized by an increase in MMP levels. In a preferred embodiment, the fusion constructs of the present invention are used to treat or prevent excessive scarring, and abnormal wound healing including keloid or hypertrophic scarring and/or chronic wounds. In a further preferred embodiment, the fusion constructs of the present invention are used to inhibit or prevent the formation of scar tissue.

A typical wound healing response is characterized by the movement of specialized cells into the wound site. Platelets and inflammatory cells are generally the first cells to arrive at the place of injury and these molecules provide important functions and chemical signals, including cytokines that are necessary for the influx of connective tissue cells and other healing factors. The term “wound” means a disruption of normal physiological structure and function. Thus, the wound healing process refers to the complex and dynamic sequence of events ultimately resulting in the restoration of physiological continuity and function.

When a wound heals, a scar usually develops in its place. During the course of normal wound healing, simple tissues such as fat, connective tissue, and epithelium are regenerated. However, because the skin is a more complex organ that is derived from two germ layers, it heals via the formation of a predominantly fibrous tissue, i.e., a scar.

In normal wound healing, the MMP proteolytic activity is controlled by various mechanisms including gene transcription, production of the enzyme, and by local secretion of endogenous TIMP inhibitors. During wound repair, a physiological balance exists between the activities of the MMP’s and the TIMPs. However, matrix metalloproteases are known to have elevated levels in chronic wounds and such high MMP concentrations are known to impair the wound healing process. Multiple cell types, including macrophages, fibroblasts, neutrophils, epithelial cells, and endothelial cells, synthesize MMP’s in the presence of specific biochemical signals such as inflammatory cytokines. MMP’s are capable of digesting almost all of the components of the extracellular matrix, which challenges the required balance between the protein degrading activities of MMPs and other cellular activity that synthesizes and deposits protein components of tissue.

FIG. 8 provides an overview of the tissue remodeling process, fibrosis and those factors involved in modulating this process. Upon an acute and chronic inflammatory reaction to a particular insult, a parasitic infection, or an autoimmune response, fibrogenic factors are expressed and secreted thus leading to the activation of fibroblasts and keratinocytes. These fibrogenic factors include, inter alia, TGF-β, IL-β, IL-1α, MOB, TGF-α, IL-4, IL-13, bFGF, TNF-α and PDGF-BB. Perhaps the two most important of these cytokines are: TNF, which is mitogenic for fibroblasts and promotes angiogenesis and is secreted by macrophages, mast cells, and T lymphocytes; and TGF-α, which is mitogenic for keratinocytes and fibroblasts, stimulates keratinocyte migration, and is secreted by macrophages, T lymphocytes, and keratinocytes. The stage involving TNF and TGF secretion marks the transition from the inflammatory phase of the wound healing process into the process of tissue reconstruction, i.e., the proliferative phase.

Upon activation, fibroblasts secrete IL-6 which, in combination with TGF-β, leads to a proliferation of the fibroblasts. TGF-β also promotes fibroblast differentiation. The result of these proliferation and differentiation processes is an overall increase in collagen, fibronectin, TIMPs, MMPs, as well as other ECM proteins, which leads to an increase in ECM production and a decrease in ECM turnover.

The present invention is based on the unexpected finding that the disclosed fusion constructs, i.e. TIMP proteins or mutants thereof, fused to a GPI-anchor, a mucin-GPI-anchor or a fractalkine-GPI-anchor can be used as a powerful agent to influence the expression level and/or activity of the cytokines and other important enzymes involved in the process of wound healing. Thus, the present invention offers effective regenerative agents and methods for controlling the process of wound healing (e.g. to influence, inhibit or prevent the formation of scar tissue) and for treating other known dysfunctions associated with the wound healing process.

Abnormal Wound Healing

Keloid and hypertrophic scarring are characterized by an accumulation of excess collagen and are distinguishable from one another by their physical appearance. Both keloid and hypertrophic scars are wounds that heal overzealously external to the skin surface. A keloid scar typically continues to enlarge beyond the size and shape of the wound, while a hypertrophic scar enlarges within the physical confines of the original wound. Hypertrophic scarring is generally observable soon after tissue injury, whereas keloid scars can form as late as one year following the time of injury. However, almost all instances of abnormal scarring are associated with physiological insults including tattoos, burns, injections, bites, vaccinations, trauma, surgery, or infection.

Hypertrophic scars and keloids can both be described as variations of the typical wound healing process. In a typical wound, anabolic and catabolic processes achieve equilibrium approximately 6-8 weeks after the original injury. During maturation of the scar, the tensile strength of the skin improves as collagen fibers are progressively cross-linked. At this point, the scar is usually hyperemic and may be thickened. However, initial scar tissue tends to subside gradually over a period of months yielding to more mature scar that is typically flat, white, pliable, and possibly stretched in appearance. Where there is an imbalance between the anabolic and catabolic phases of the wound healing process, more collagen is produced than is degraded, and the scar can therefore grow in all directions.

A single, optimal method for treating hypertrophic and keloid scar tissue has not yet been developed, thus the recurrence rate of these abnormal scars is significant.

In summary, cytokines and specific enzymes, including the MMPs and TIMPs, play a crucial role in the process of wound healing and in the formation of scar tissue. Furthermore, an abnormal expression in the levels of MMPs and cytokines are often associated with abnormal wound healing.

Thus, the present invention offers effective regenerative agents and methods for controlling the process of wound healing and/or to treat dysfunctions commonly associated with wound healing. Specifically, the fusion constructs of the present invention can be utilized to effectively control, alter, inhibit or even prevent these undesirable processes. The fusion constructs of the present invention can be formulated as a pharmaceutical and administered at the site of injury. In one embodiment, the site of injury is created by surgery, a burn, an injection, a bite, a vaccination, a trauma, surgery, or infection. In another embodiment, the fusion construct used for the preparation of the medicament to be applied to the site of injury is selected from the group consisting of TIMP-1-GPI, TIMP-2-GPI, TIMP-3-GPI, TIMP-4-GPI, TIMP-1-muc-GPI, TIMP-2-muc-GPI, TIMP-3-muc-GPI and TIMP-4-muc-GPI or mutants thereof.

Formulation of the TIMP Constructs and Modes of Administration

Pharmaceutical compositions based on the TIMP constructs of the present invention may be formulated in a conventional manner using one or more physiologically acceptable carriers or excipients. Techniques and formulations generally may be found in *Remington's Pharmaceutical Sciences*, Meade Publishing Co., Easton, Pa. For the purposes of injection, the compounds of the invention can be formulated in a liquid solution, preferably in a physiologically compatible buffer such as Hank's solution or Ringer's solution. In addition, the compounds may be formulated in solid form and redissolved, or suspended immediately prior to use. Lyophilized forms are also suitable.

In addition to these formulations, the compounds may also be formulated as a depot preparation. These long acting depot formulations may be administered by implantation (for example, subcutaneously or intramuscularly) or by injection. Thus, the compounds may be formulated with suitable polymeric or hydrophobic materials (for example, as an emulsion in an acceptable oil) or as an ion exchange resin, or as a sparingly soluble derivative, such as a sparingly soluble salt. Other suitable delivery systems include microspheres, which offer the possibility of a local and noninvasive delivery of drugs over an extended period of time. This particular technology utilizes microspheres having a precapillary size that can be injected via a coronary catheter into any selected part of a tissue, e.g. the heart or other organs, without causing a resulting inflammation or ischemia. The administered therapeutic is slowly released from these microspheres and readily taken up by cells present in the surrounding tissue (e.g. injured or cancerous cells).

For topical administration, the oligomers of the invention can be formulated into ointments, salves, gels, or creams generally known in the art. A wash solution containing the oligomer can be used locally to treat an injury or inflammation or to generally accelerate the healing process.

The TIMP constructs of the present invention may be combined when preparing a medicament, so that the resulting medicament comprises more than one, preferably two, and even more preferably three different TIMP constructs. With this approach, the amplified and novel bioactivities of the different members of the TIMP family may be preferentially combined and targeted to the cell surface, which can lead to a synergistic effect. For example, the TIMP-1 fusion constructs inhibits most MMPs, except MMP-2 and MMP14. Therefore, any of the TIMP-1 constructs may be combined with any of the TIMP-2 or TIMP-4 constructs which both preferentially inhibit MMP-2. Therefore, by means of this combination, a more complete inhibition of the MMP family can be achieved.

In one embodiment, the formulations of the present invention therefore comprise a TIMP-1 construct, or a TIMP-2 and/or a TIMP-4 construct. In a preferred embodiment, the formulation comprises a TIMP-1 construct selected from the group consisting of a truncated TIMP-1-GPI as encoded by SEQ ID NO:1, a truncated TIMP-1-frac-GPI as encoded by SEQ ID NO:5, and a truncated TIMP-1-muc-GPI as encoded by SEQ ID NO:2, and a TIMP-2 and/or a TIMP-4 construct. Preferably, the TIMP-2 construct is encoded by SEQ ID NO:3.

In a further embodiment, the formulation comprises a TIMP-3 construct of the present invention, preferably that encoded by SEQ ID NO:4, which inhibits TACE together with at least one of the TIMP constructs selected from the group consisting of a truncated TIMP-1-GPI as encoded by SEQ ID NO:1, a truncated TIMP-1-frac-GPI, a truncated TIMP-1-muc-GPI, a TIMP-2 and TIMP-4 construct. Preferably, the TIMP-1 and TIMP-2 constructs are encoded by SEQ ID NOs: 1, 2, 3 and 5, respectively.

A. To demonstrate re-incorporation of GPI-TIMP-1 protein into cell membranes, purified TIMP-1-GPI or control rhTIMP-1 was added to native RCC-26, RCC-53 and A498 cells. TIMP-1 was detected on the cell surface by FACS analysis. Grey histograms are the isotype control staining, solid-line histograms represent TIMP-1 antibody staining.

B. To demonstrate GPI-linkage following incubation with 200 ng/ml or 700 ng/ml of TIMP-1-GPI or rhTIMP-1, cells were treated with 60 ng/ml PLC and then subjected to FACS analysis. Grey histograms represent the isotype control.

C. Human TIMP-1 ELISA was used to determine the amount of TIMP-1 protein released from TIMP-1-GPI-treated RCC cells (as shown in B) following PLC-digestion.

Figure 2:
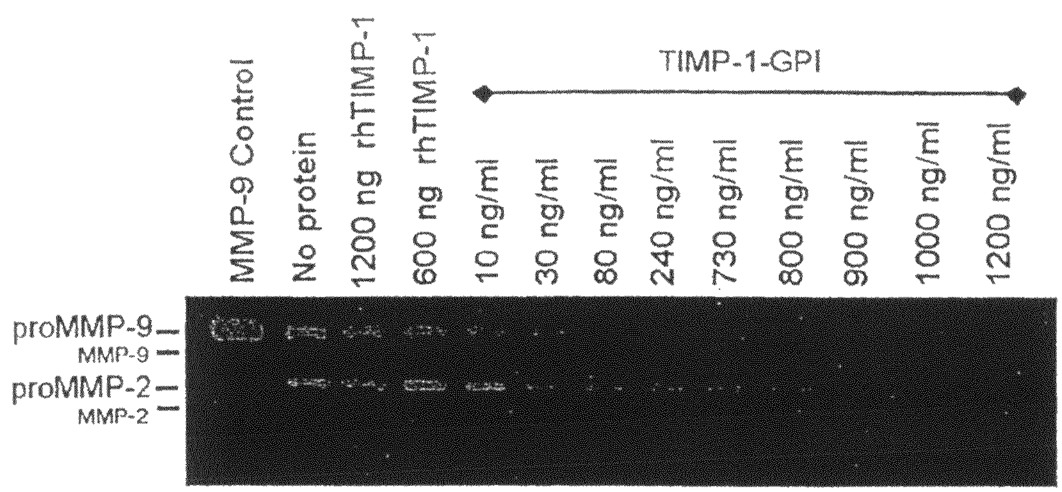

FIG. 2. TIMP-1-GPI inhibits release of proMMP-2 and proMMP-9 from RCC-53 cells.

Zymography was used to study the secretion of MMP-2 and MMP-9 proteins from RCC-53. The cells were treated with increasing amounts of TIMP-1-GPI, or control rhTIMP-1, and after 48 h the serum free culture supernatant was removed and analyzed by gelatinase zymography.

Figure 3:
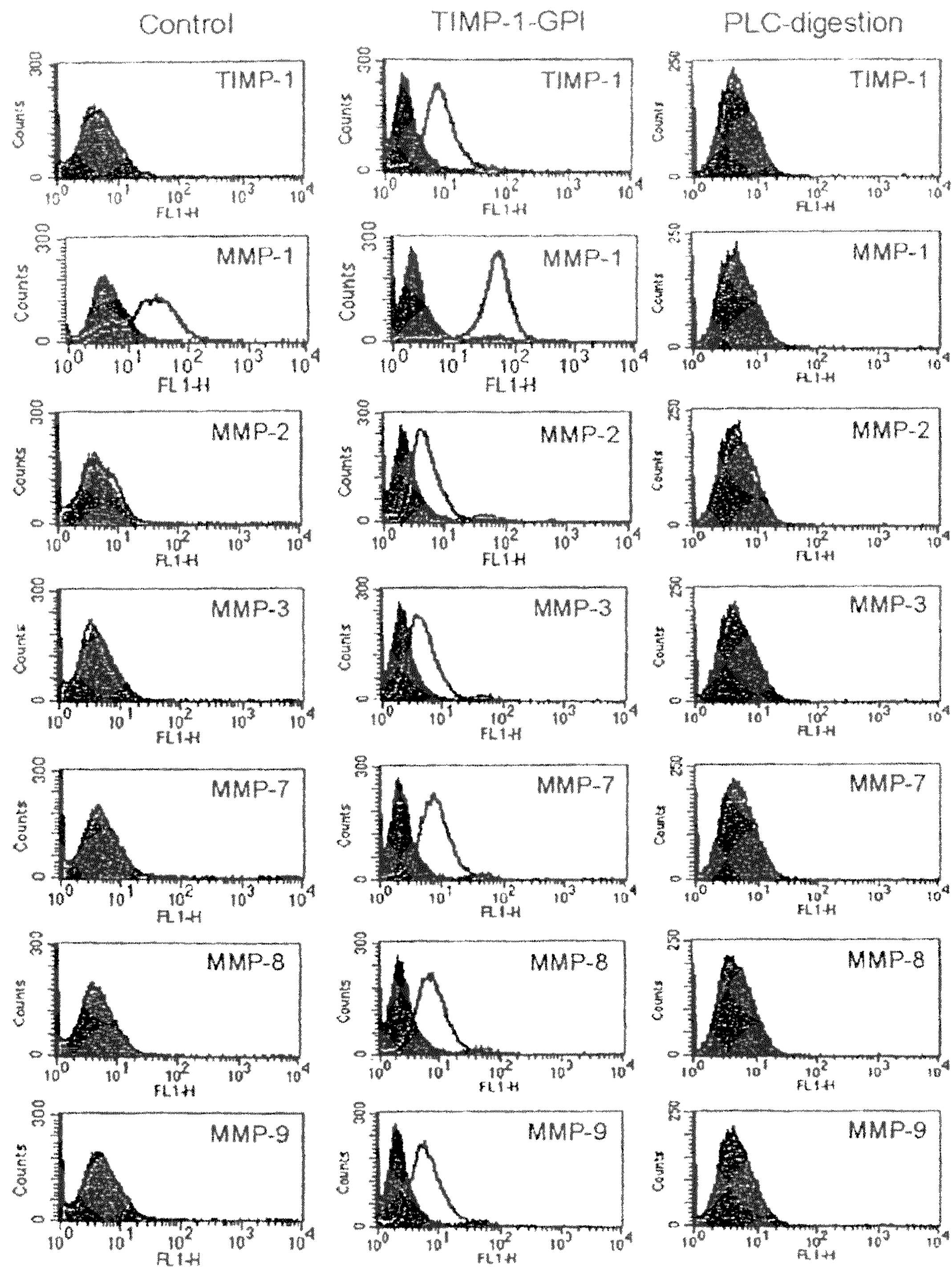
Figure 3:
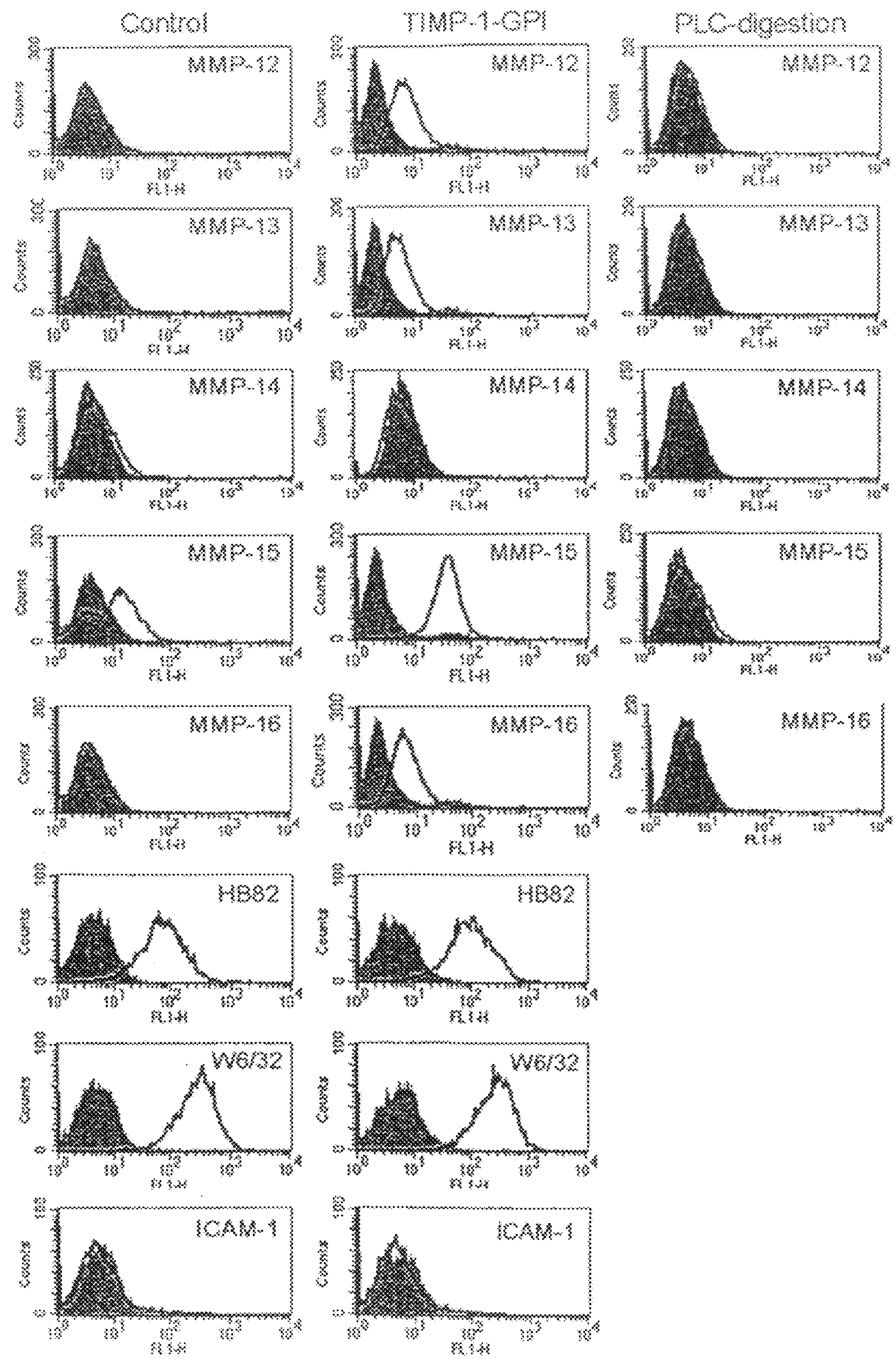
Figure 3:
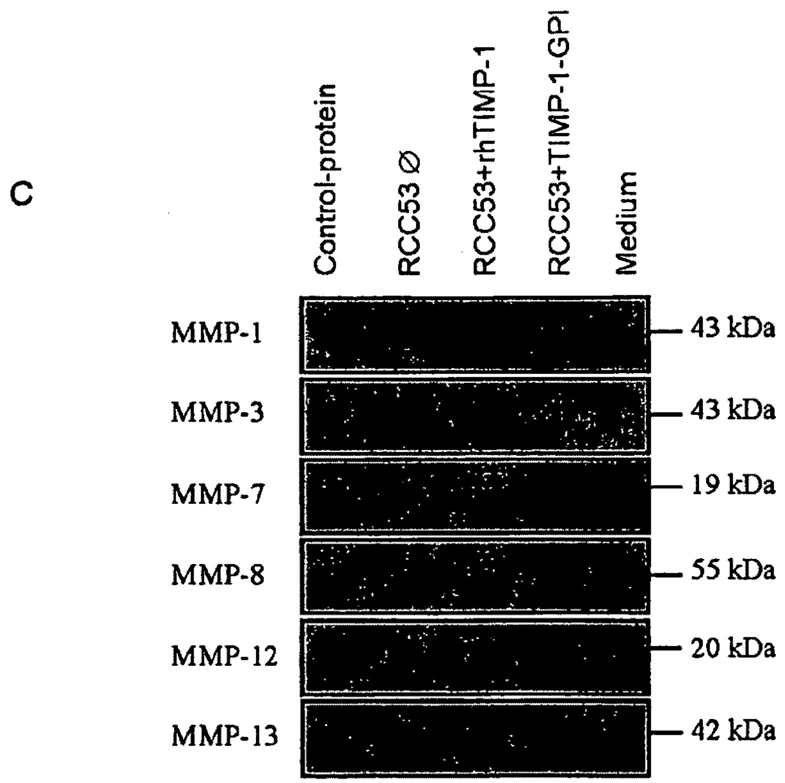
Figure 3:
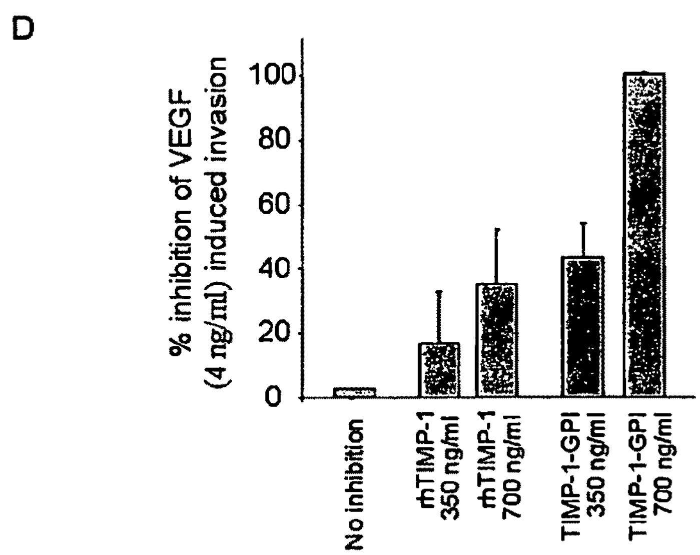

FIG. 3. Surface expression of MMPs after treatment with TIMP-1-GPI.

Figure 1:
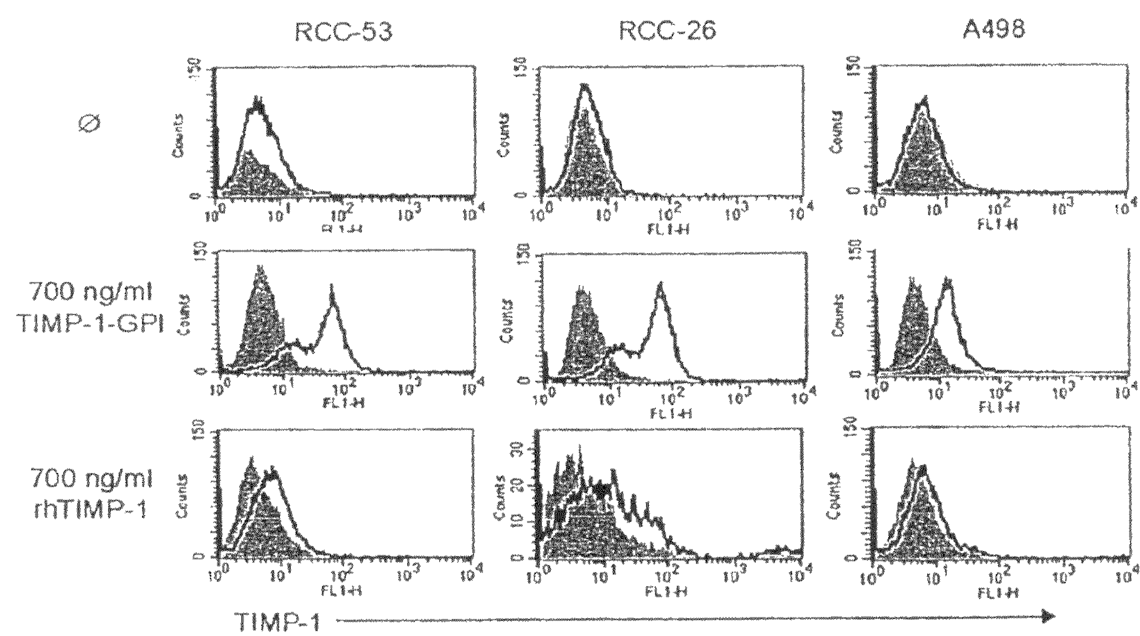
FIG. 1. TIMP-1-GPI incorporation into cell membranes of RCCs.
Figure 1:
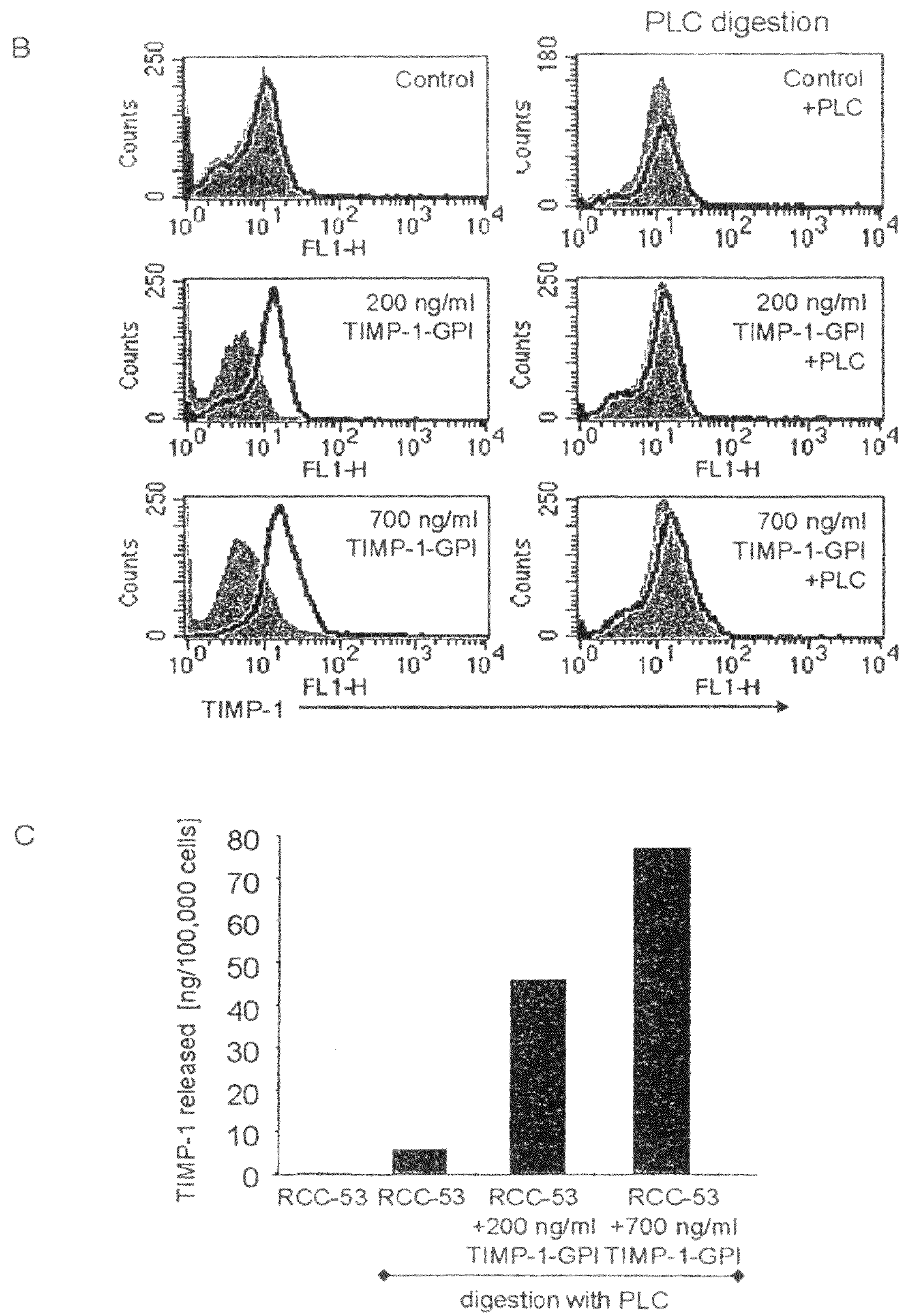

Following incubation of RCC-53 cells with 700 ng/ml of TIMP-1-GPI protein for 24 h FACS was performed using specific antibodies directed against: (A) TIMP-1, MMP-1, MMP-2, MMP-3, MMP-7, MMP-8 and MMP-9, or (B) MMP-12, MMP-13, MMP-14, MMP-16, HLA-A2 (HB82), pan HLA Class I (W6/32) and ICAM-1. As an additional control, the TIMP-1-GPI was cleaved from the surface after one hr by PLC treatment (see FIG. 1). Grey histograms are the isotype control staining, solid-line histograms represent TIMP-1-GPI treated samples.

C. The secretion of a series of MMPs from RCC53 was tested using Western blot and monoclonal antibodies directed against MMP-1, MMP-3, MMP-7, MMP-8, MMP-12 and MMP-13. Culture media (serum free) was taken 24 hr after treatment of RCC-53 with 700 ng/ml of either rhTIMP-1 or TIMP-1-GPI and compared to untreated control cells.

D. The effect of cell surface sequestering of MMPs on RCC-53 invasion through Matragel model basement membrane was assessed. Optimal migration of the RCC-53 cells to VEGF (4 ng/ml) was set as baseline or "zero" and the 100% inhibition value set to migration value seen for untreated RCC-53 cells with no VEGF signal. The RCC-53 cells were pretreated with 350 ng/ml or 700 ng/ml of either rhTIMP-1 or TIMP-1-GPI. After one hr the cells were washed and applied to the migration chamber. The effect on migration was then assessed. Data presented represent an average from four wells and two experiments.

Figure 4:
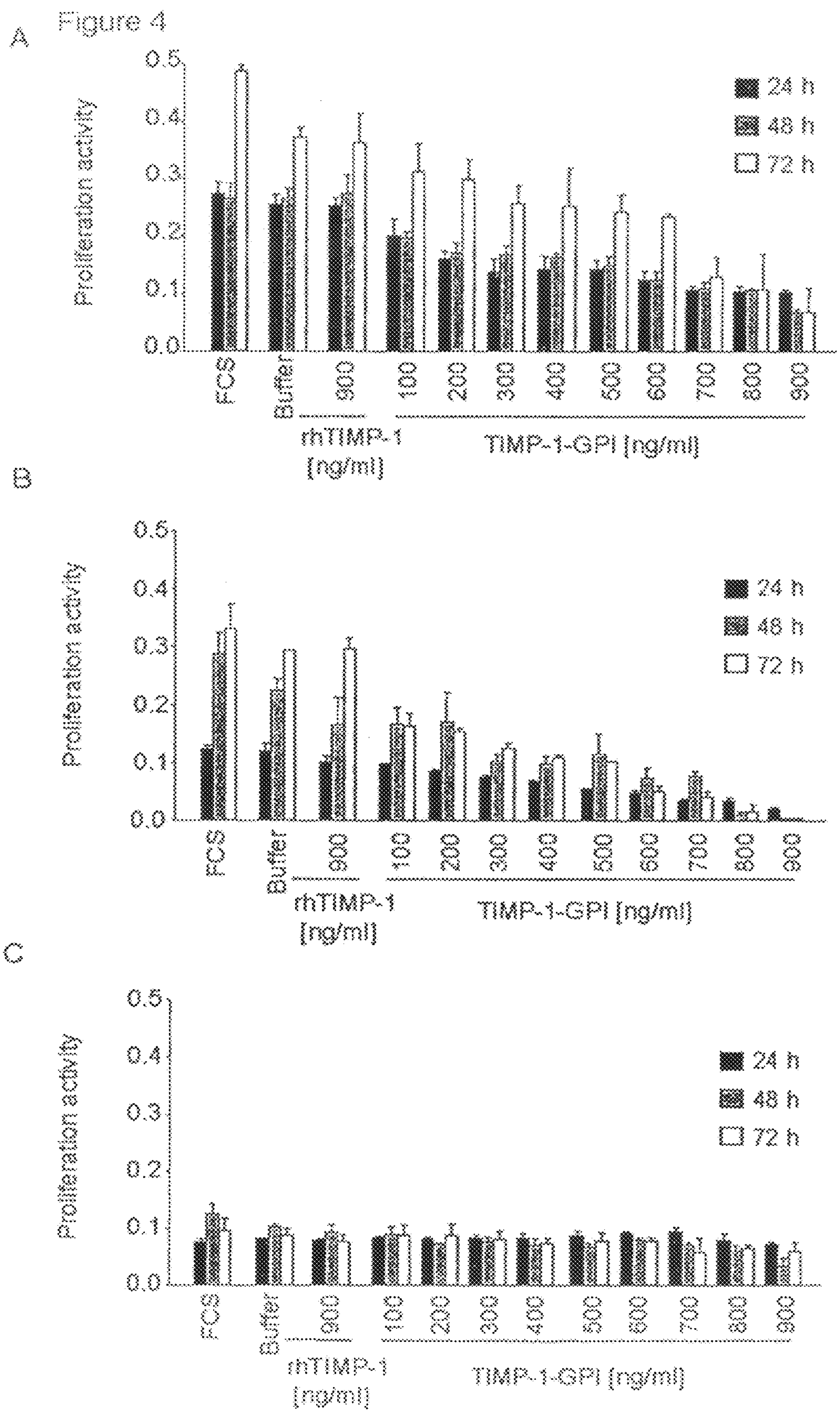

FIG. 4. Effect of rhTIMP-1 and TIMP-1-GPI protein on the proliferation of the RCC lines.

The effect of increasing levels of TIMP-1-GPI or rhTIMP-1 control protein on the proliferation of RCC-53 (A), A498 (B) and RCC-26 (C) was measured using an MTT assay. MTT was added after 24 h, 48 h or 72 h as indicated.

Figure 5:
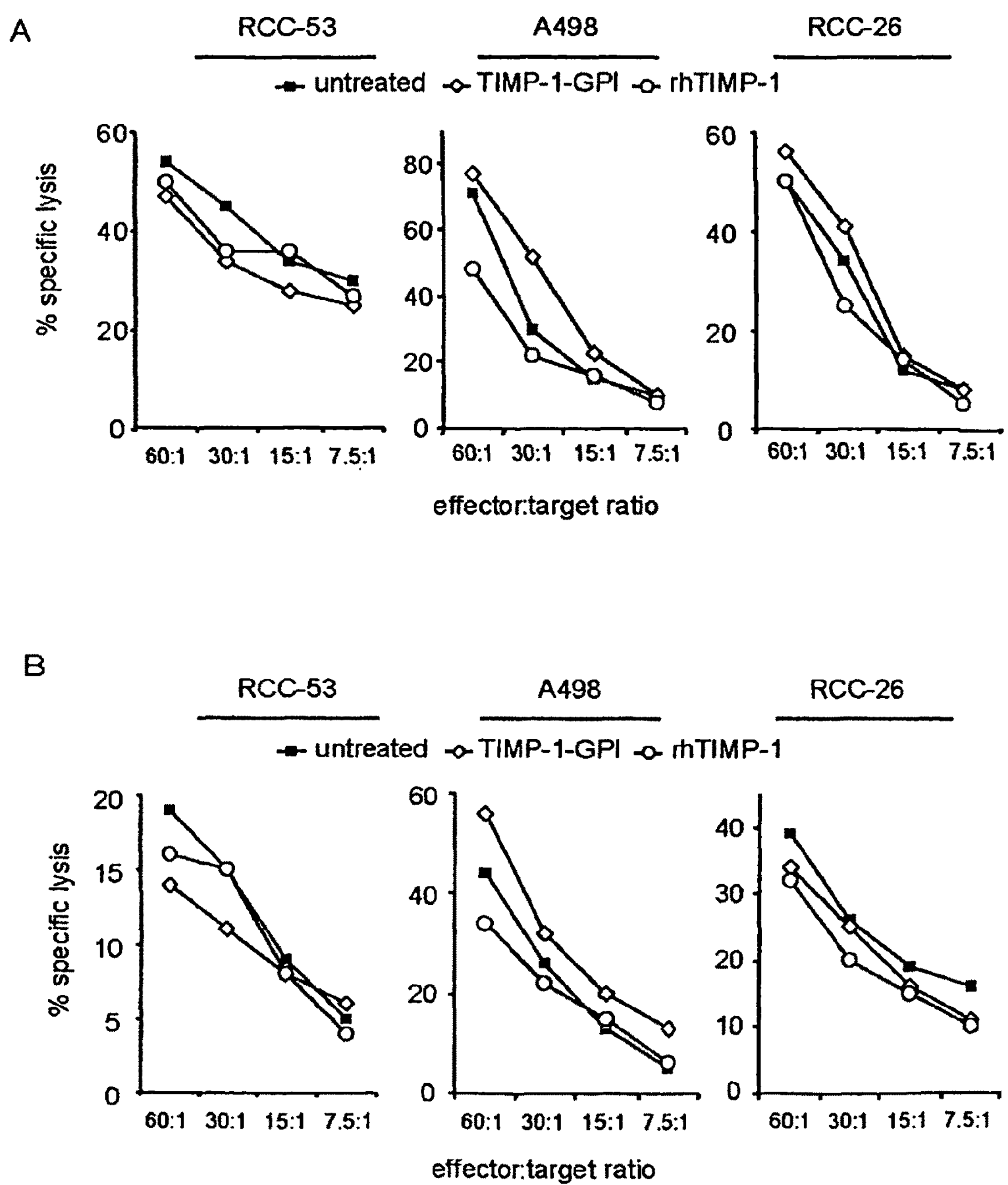

FIG. 5. TIMP-1-GPI does not influence RCC susceptibility to perforin mediated apoptosis.

RCC cells were left untreated (■), treated with 700 ng/ml TIMP-1-GPI (◇) or rhTIMP-1 protein (○) for 24 h and incubated with either the CTL JB4 (A) or NK-lines (B) (NKL for RCC-53 and A498, or NK-92 for RCC-26). Shown are representative examples of three independent experiments with similar results.

Figure 6:
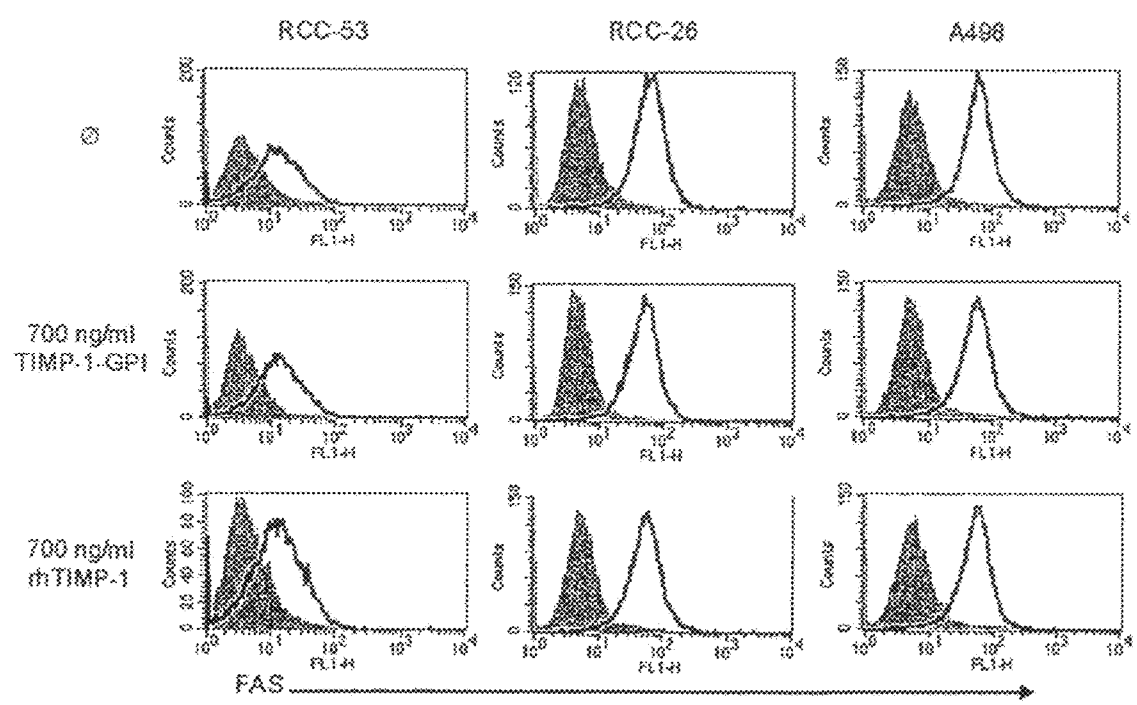
Figure 6:
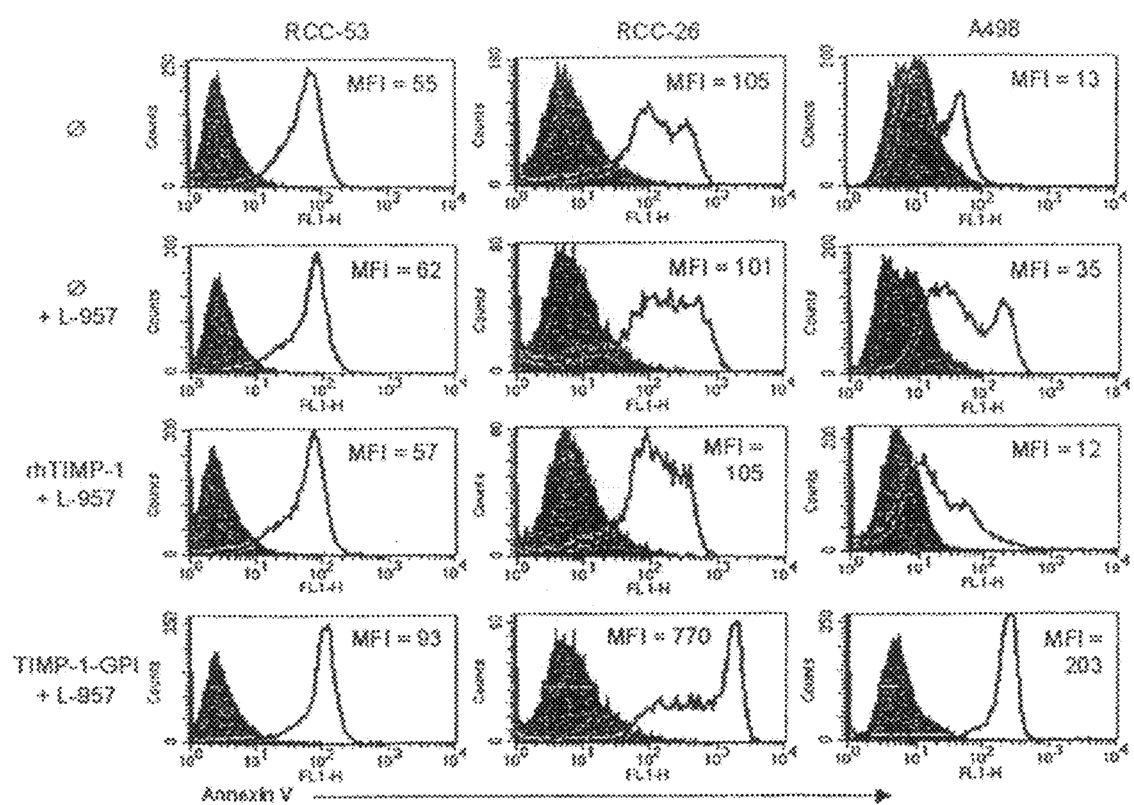
Figure 6:
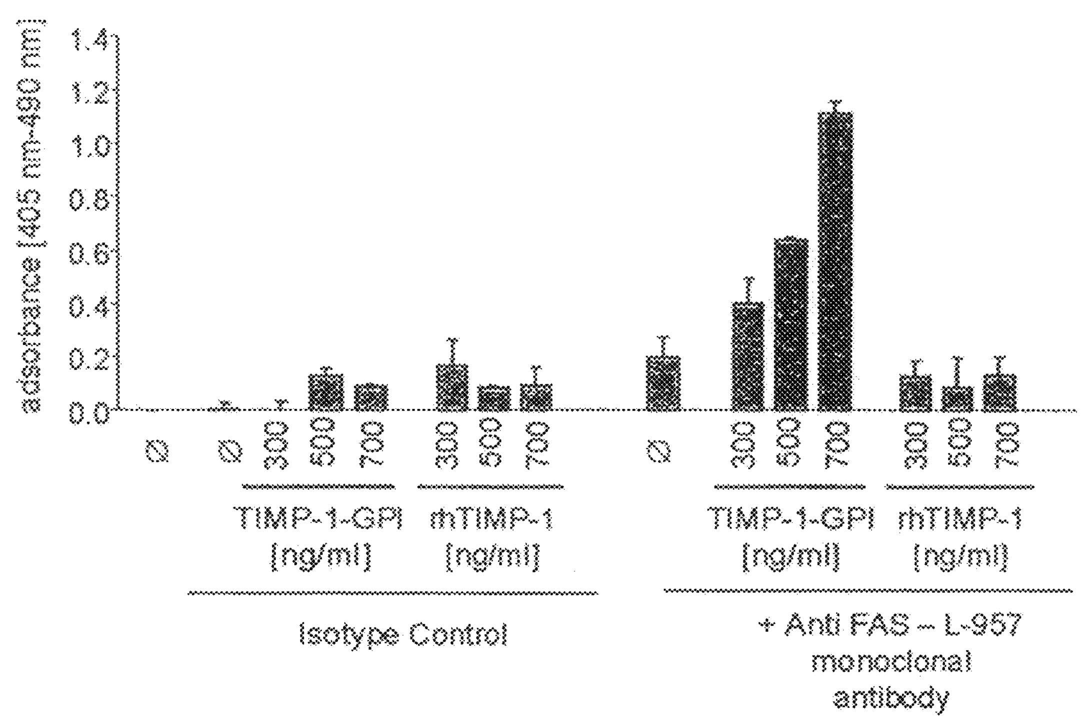

FIG. 6. TIMP-1-GPI does not increase FAS expression but renders cells sensitive to FAS-induced apoptosis.

A. RCC-53, RCC-26 or A498 cells were treated or untreated with 700 ng/ml TIMP-1-GPI or rhTIMP-1 for 24 h, and were stained with anti-human FAS (L-958) and analyzed for FAS surface expression by flow cytometry. Monoclonal antibody isotype control stains are shown as grey histograms.

The three RCC cell lines were treated with TIMP-1-GPI or rhTIMP-1 followed by L-957 incubation. Binding of annexin V-fluoroisothiocyanate (FITC) was used to detect viable and early apoptosis by flow cytometry.

The low level of apoptosis in the RCC-53 cells in (B) was verified using a more sensitive cytoplasmatic nucleosome ELISA. Increasing levels of apoptosis were detected after L-957 incubation with increasing levels of TIMP-1-GPI—but not rhTIMP-1.

Figure 7:
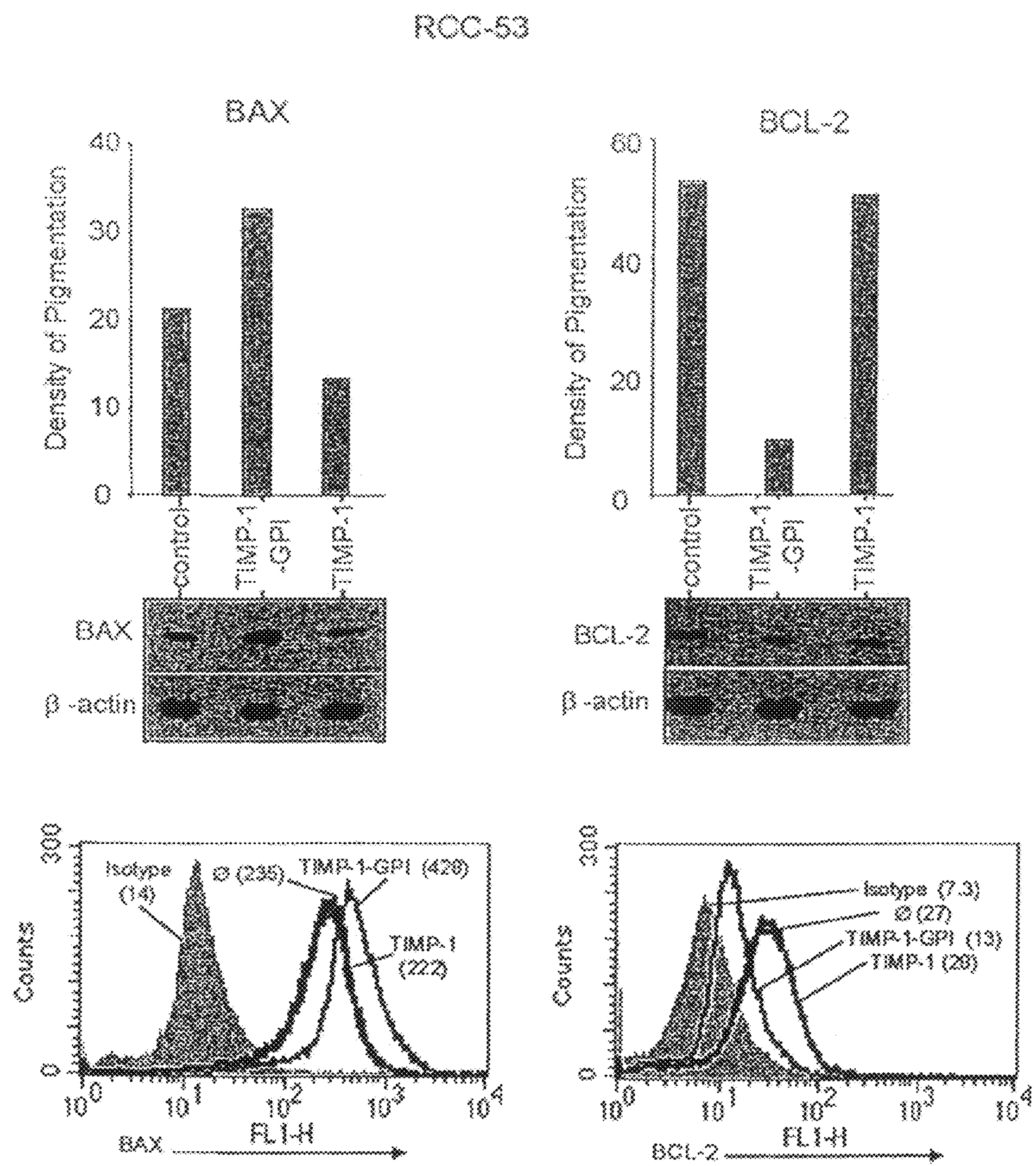
Figure 7:
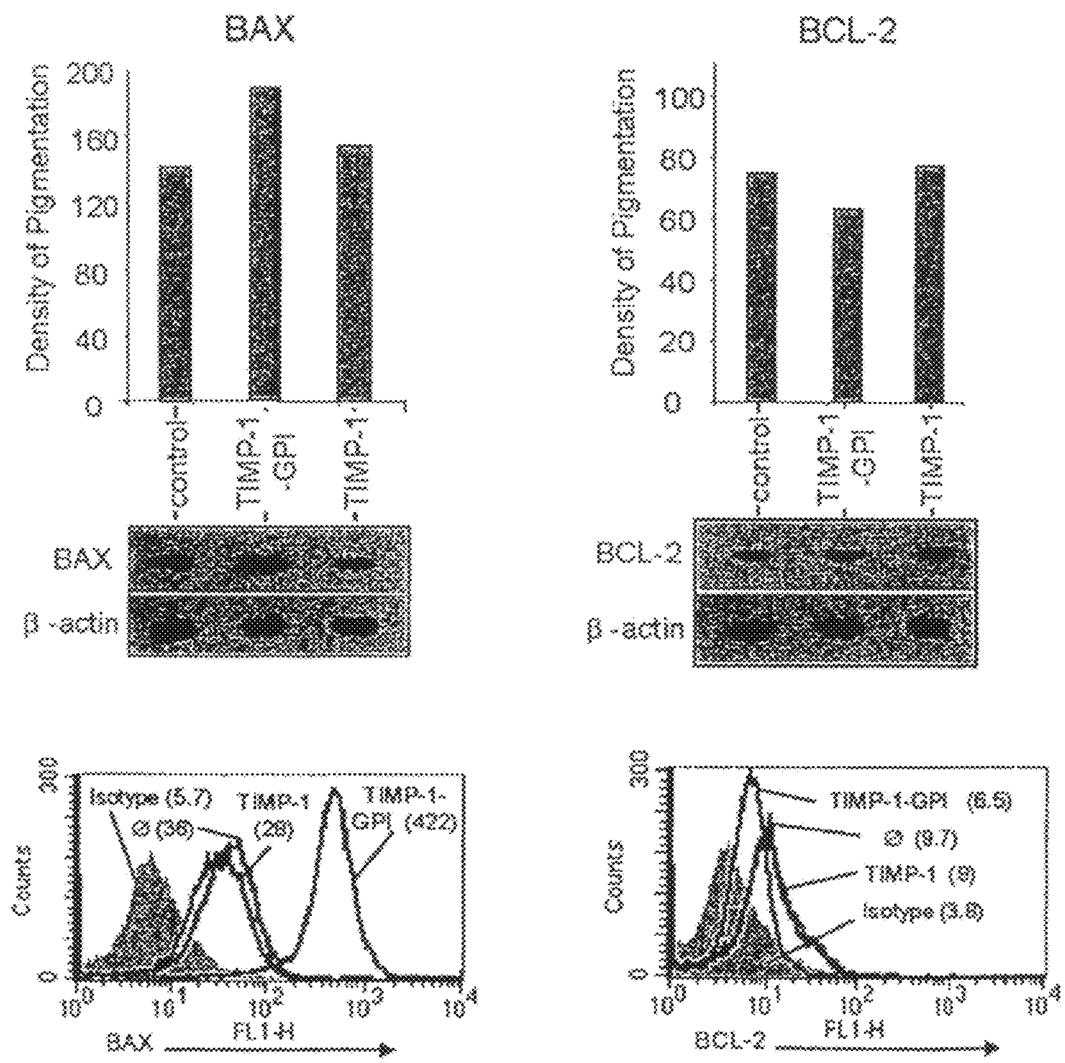
Figure 7:
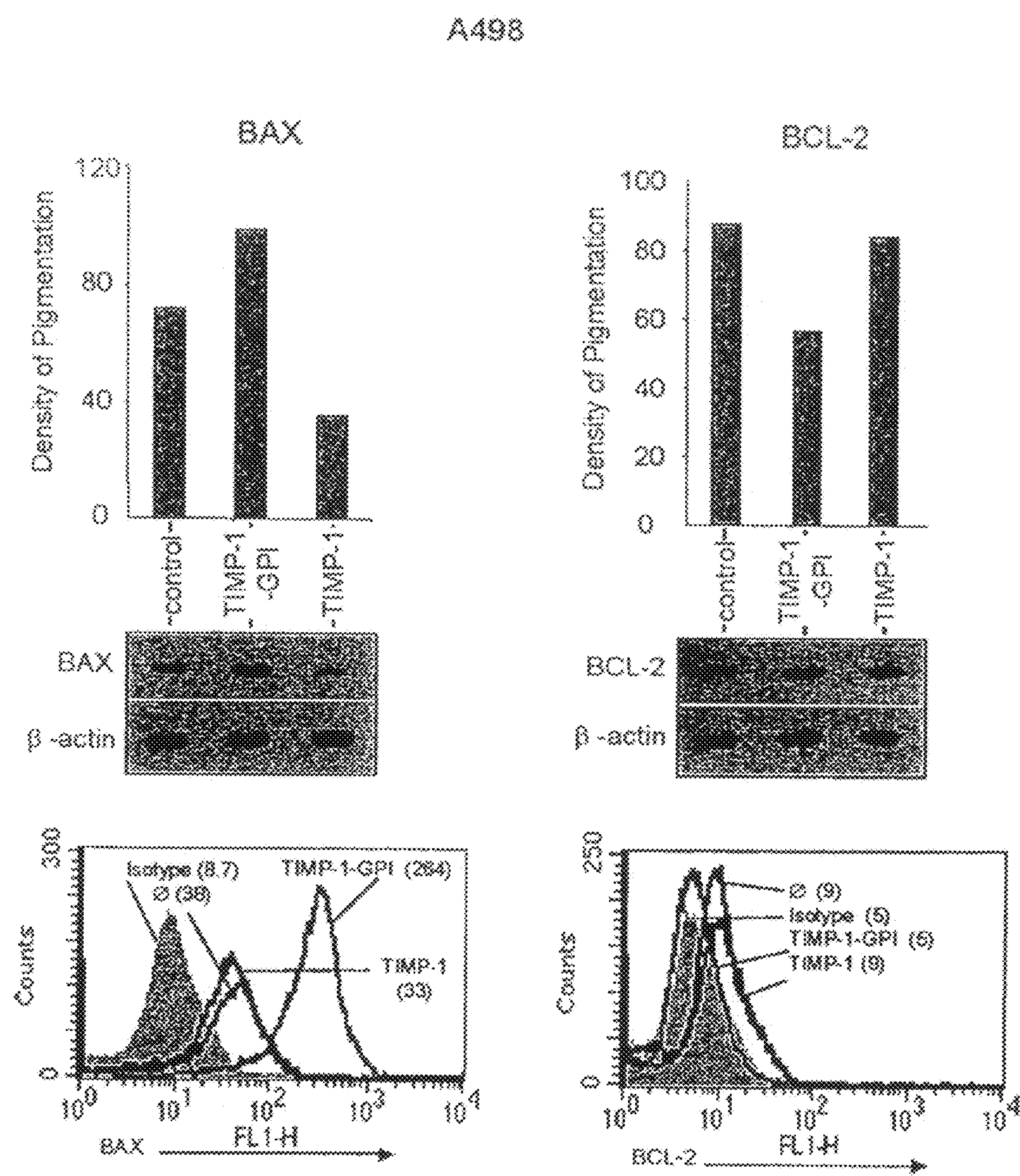

FIG. 7. BCL-2 and BAX expression in RCCs following treatment with TIMP-1-GPI or rhTIMP-1, analysed by internal FACS staining and Western blot.

RCC-53 (A), RCC-26 (B) and A498 (C) cells were preincubated with TIMP-1-GPI or rhTIMP-1 for 24 h, then treated with L-957 activating FAS-antibody for an additional 16 h. Cells were then analyzed with anti-BCL-2 and anti-BAX monoclonal antibodies using flow cytometry. In parallel proteins were extracted and measured by Western blot. The signals derived from BAX and BCL-2 were normalized to β-actin levels following densitometry. FACS results are presented as histograms with values in parenthesis corresponding to the MFI of either BCL-2 or BAX or corresponding isotype antibodies.

Figure 8:
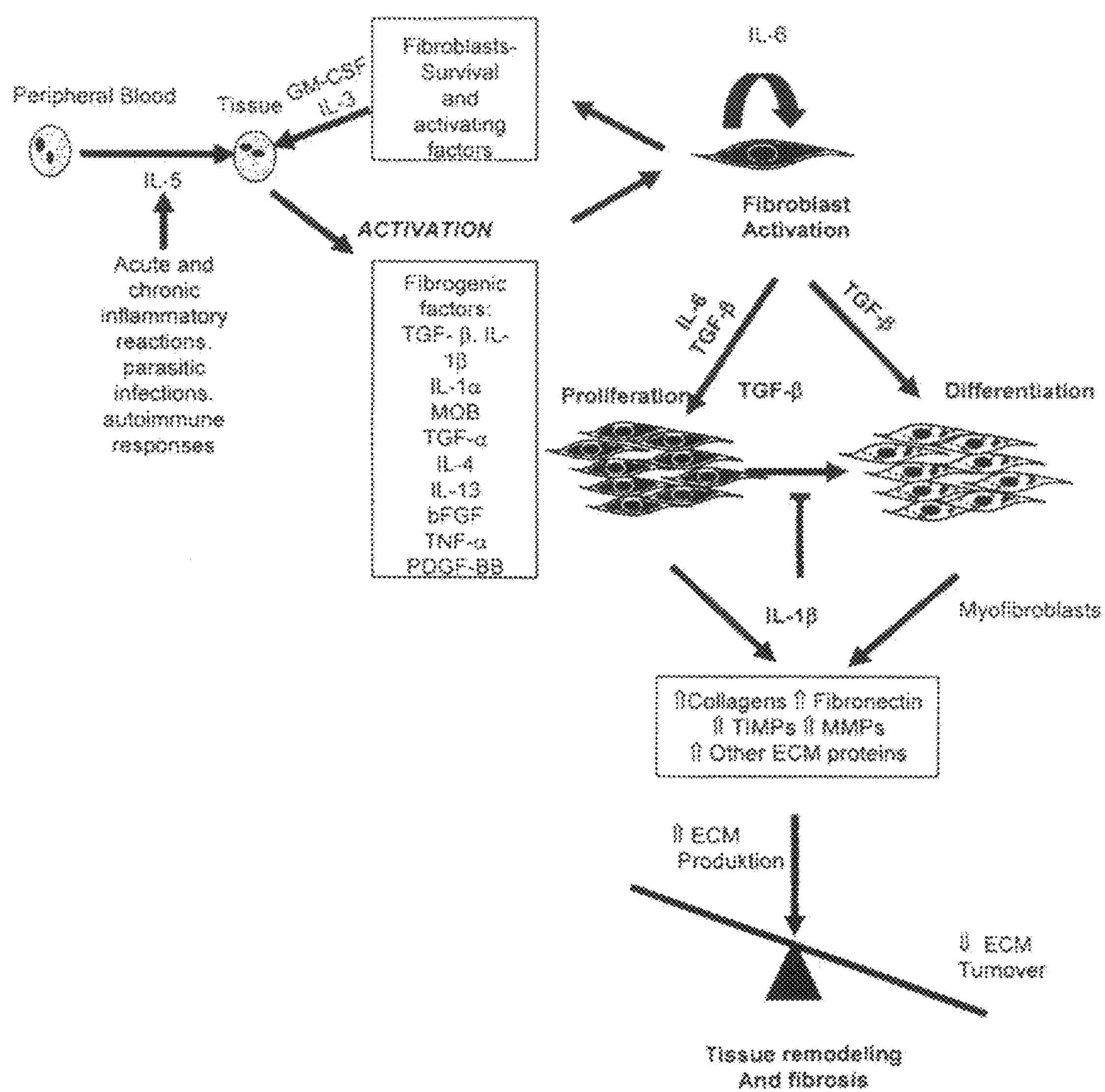

FIG. 8: Overview of tissue remodeling and fibrosis

A schematic diagram depicting the complex interaction of factors involved in the delicate balance of ECM production and turnover during the wound healing process.

Figure 9:
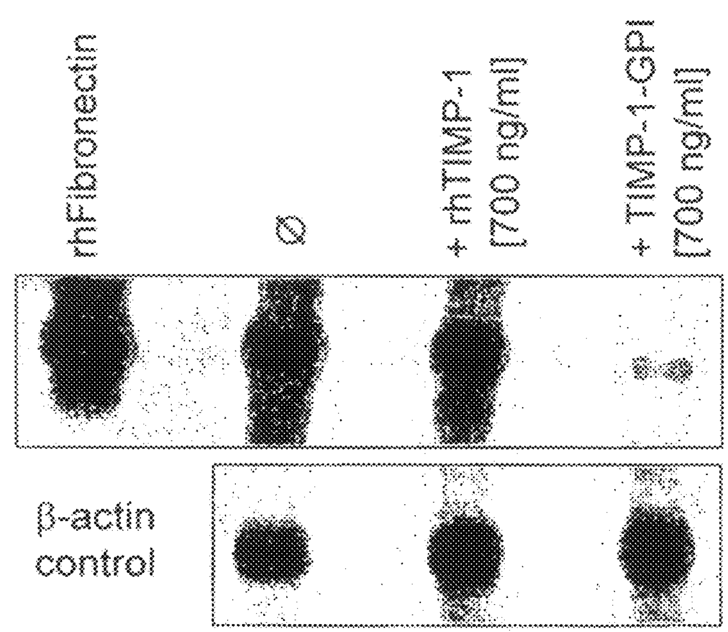

FIG. 9: Effect of TIMP fusion constructs on fibronectin production of fibroblasts in the presence of rhTIMP-1

Confluent fibroblasts were cultured in the presence or absence of rhTIMP-1 and TIMP-1-GPI; expressed and secreted fibronectin was quantified by Western blot analysis using anti fibronectin antibodies (β-actin served as a control). rhTIMP-1 (at 700 ng/ml) did not lead to any significant decrease in fibronectin expression, while TIMP-1-GPI (at 700 ng/ml) strongly reduced the fibronectin that was secreted by the fibroblasts.

Figure 10:
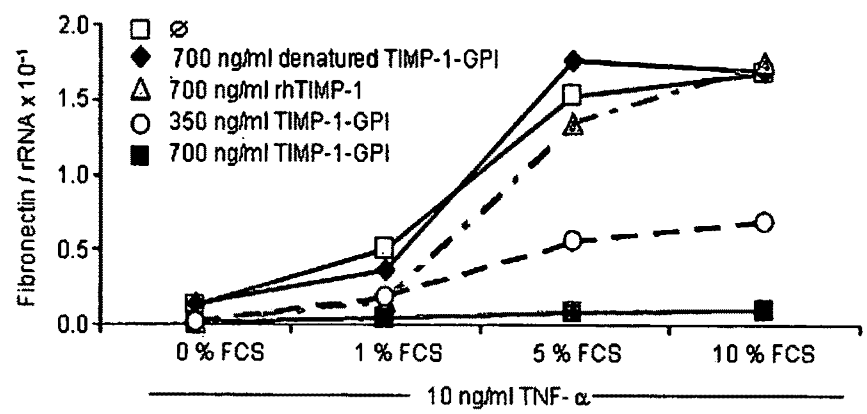
Figure 10:
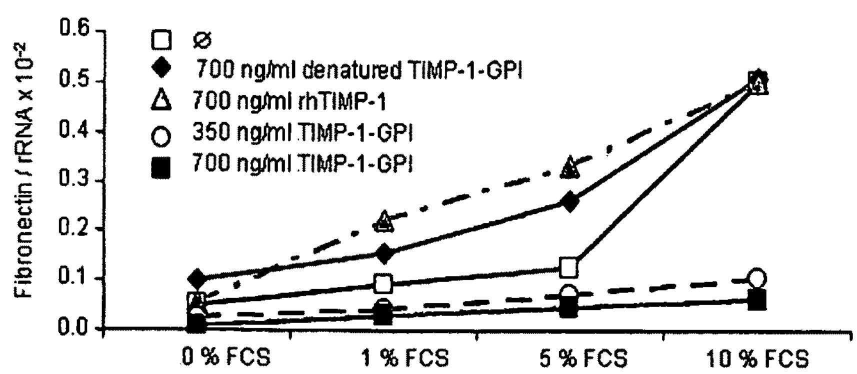

FIG. 10. Effect of TIMP fusion constructs on fibronectin production of fibroblasts in the presence of TNF-α

Fibroblasts were cultured in the presence (FIG. 10A) or absence (FIG. 10B) of 10 ng/ml of the fibroblast activating TNF-α together with 350 ng/ml TIMP-1-GPI or 700 ng/ml TIMP-1-GPI, denatured TIMP-1-GPI and rhTIMP-1-GPI, respectively. At a concentration of 350 ng/ml of TIMP-1-GPI, the transcribed fibronectin RNA was significantly reduced, independently of whether TNF-α was present in the medium.

Figure 11:
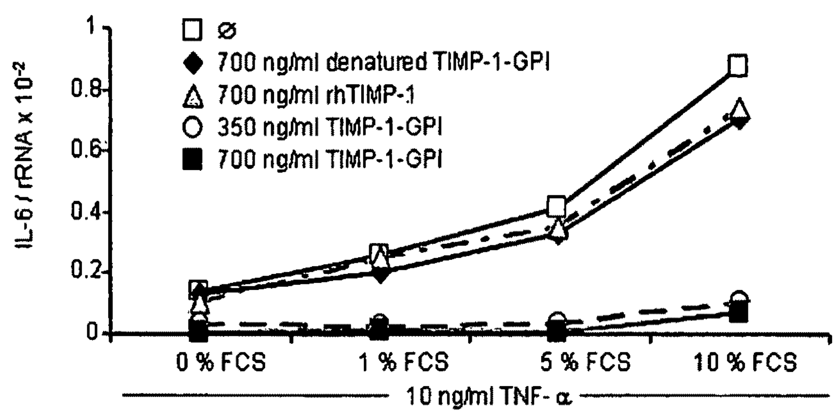
Figure 11:
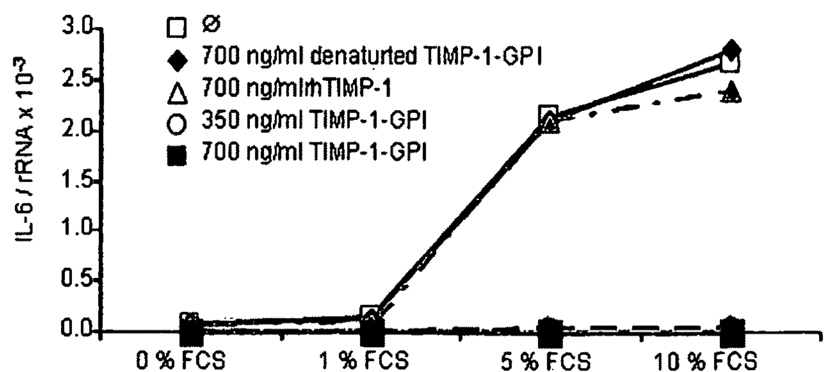

FIG. 11. Effect of TIMP fusion constructs on IL-6 production of fibroblasts

Fibronectin RNA as transcribed by fibroblasts was assessed by Northern blot analysis, using a probe for IL-6 RNA. Thus, fibroblasts were cultured in the presence (FIG. 11A) or absence (FIG. 11B) of 10 ng/ml of the fibroblast activating TNF-α together with 350 ng/ml TIMP-1-GPI or 700 ng/ml TIMP-1-GPI, denatured TIMP-1-GPI and rhTIMP-1-GPI, respectively. At a concentration of 350 ng/ml of TIMP-1-GPI, the transcribed IL-6 RNA was strikingly reduced, independently of whether TNF-α was present in the medium.

Figure 12:
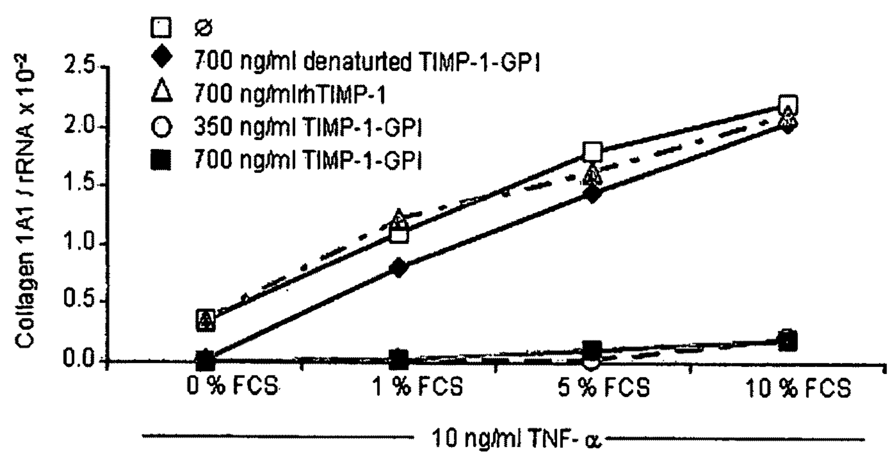
Figure 12:
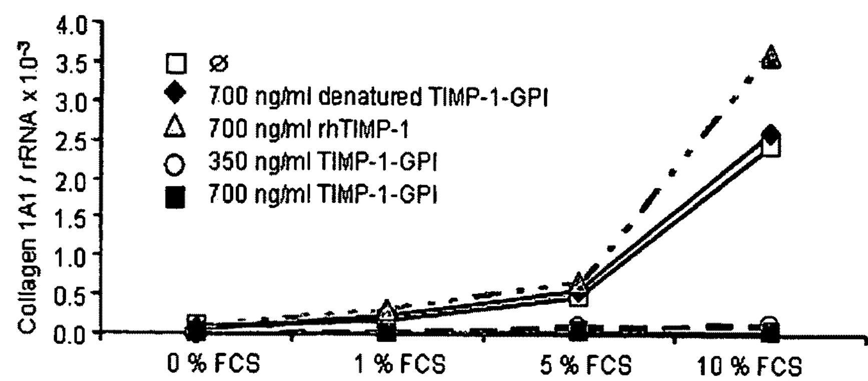
Figure 12:
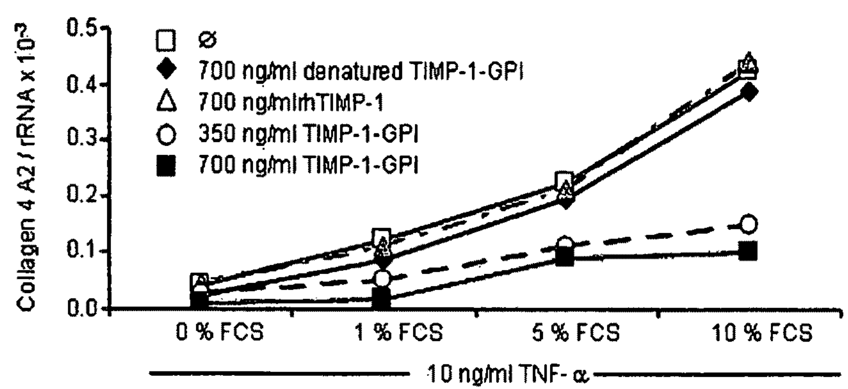
Figure 12:
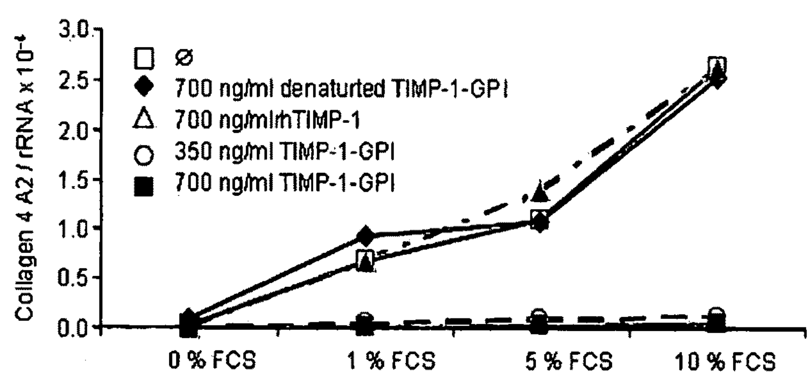
Figure 12:
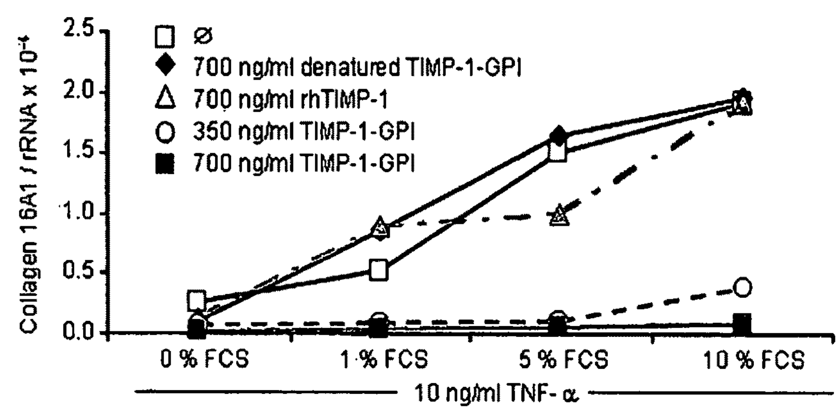
Figure 12:
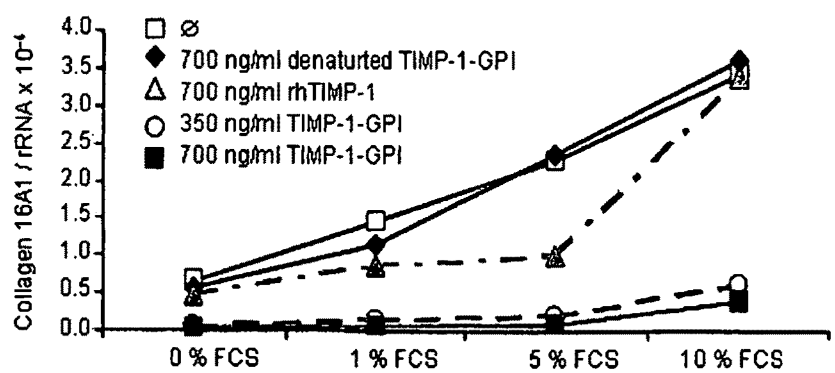

FIG. 12. Effect of TIMP fusion constructs on collagen production of fibroblasts Fibronectin RNA as transcribed by fibroblasts was assessed by Northern blot analysis, using probes for Collagen 1A1 (FIGS. 12A and B), Collagen 4A2 (FIGS. 12C and D), and Collagen 16A1 (FIGS. 12E and F), respectively. Thus, fibroblasts were cultured in the presence (FIGS. 12A, C, E) or absence (FIGS. 12B, D, F) of 10 ng/ml of the fibroblast activating TNF-α together with 350 ng/ml TIMP-1-GPI or 700 ng/ml TIMP-1-GPI, denatured TIMP-1-GPI and rhTIMP-1-GPI, respectively. At a concentration of 350 ng/ml of TIMP-1-GPI, all three transcribed collagen RNAs were significantly reduced, independently of whether TNF-α was present in the medium.

Figure 13:
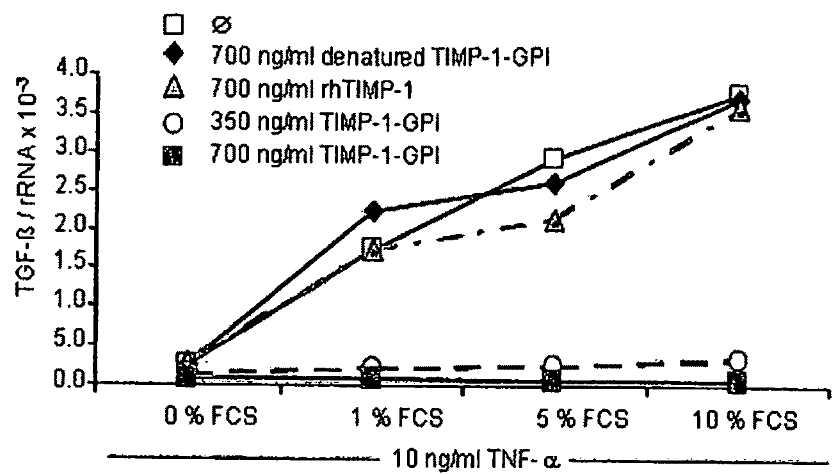
Figure 13:
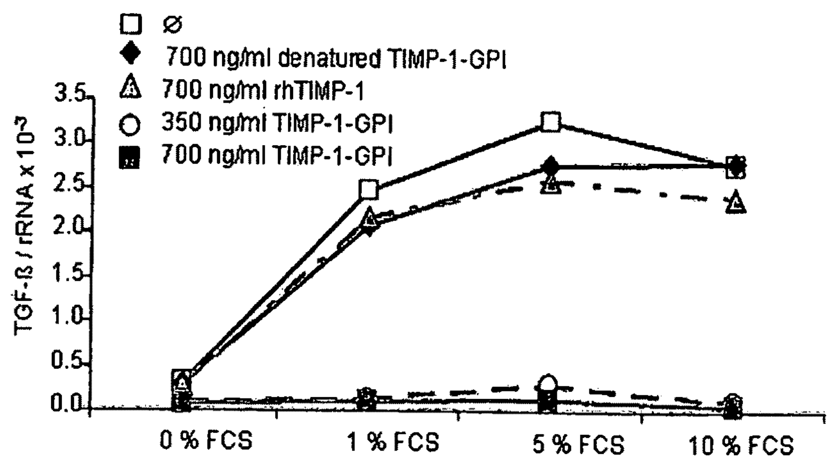

FIG. 13. Effect of TIMP fusion constructs on TGF-β production of fibroblasts Fibronectin RNA as transcribed by fibroblasts was assessed by Northern blot analysis, using probes for TGF-β. Thus, fibroblasts were cultured in the presence (FIG. 13A) or absence (FIG. 13B) of 10 ng/ml of the fibroblast activating TNF-α together with 350 ng/ml TIMP-1-GPI or 700 ng/ml TIMP-1-GPI, denatured TIMP-1-GPI and rhTIMP-1-GPI, respectively. At a concentration of 350 ng/ml of TIMP-1-GPI, almost no TGF-β RNA could be detected, independently of whether TNF-α was present in the medium, and independently of the FCS content of the medium.

EXAMPLES

In the following examples, the anti-tumor effects of the GPI-anchored TIMP on cancer cells are described in more detail. Although the experiments described are carried out with human TIMP-1, the invention shall not be limited on this type of TIMP.

In the following examples, a GPI-anchor was fused to TIMP-1 to focus defined concentrations of this inhibitory protein on the surface of three renal cell carcinoma (RCC) cell lines (RCC-26, RCC-53 and A498) independently of cell surface protein-protein interactions. As shown in the following, exogenously added TIMP-1-GPI efficiently inserted into the RCC cell membrane and dramatically altered the association of MMPs with the cell surface. TIMP-1-GPI treatment inhibited RCC proliferation and rendered the normally FAS-resistant RCC cells sensitive to FAS-induced apoptosis but did not alter perforin-mediated lysis by cytotoxic effector cells. The increased sensitivity to FAS-mediated apoptosis correlated with an alteration in the balance of pro- and anti-apoptotic BCL-2-family proteins.

The RCC-26 (Schendel et al., 1993) and RCC-53 cell lines were established from local patients with stage I and stage IV clear cell carcinomas, respectively. Thereby, they represent the two clinical extremes of RCC. Tumor-infiltrating CTL were isolated from tumor of both patients. Although these naturally occurring effector cells were unable to control tumor growth in vivo, surface marker staining of RCC-26 and RCC-53 revealed good surface expression of MHC class I, and both lines were shown to induce allo- and anti-tumor-specific CTL in vitro ((Schendel et al., 2000) and DJS, unpub. observation). A498 was originally isolated from the tumor of a 52 year old male and is a well studied example of RCC (Giard et al., 1973).

Example 1

Incorporation of Exogenously Added TIMP-1-GPI into the Surface of RCC-53

GPI-anchored TIMP-1 protein was generated and isolated as previously described (Djafarzadeh et al., 2004). The incorporation of purified GPI-TIMP-1 protein into the surface membranes of RCC-53, RCC-26 or A498 RCC cell lines was demonstrated by incubation of the cell lines with 700 ng/ml of purified TIMP-1-GPI or recombinant human (rh)TIMP-1 control protein for one hr. Surface associated TIMP-1 protein was then detected using FACS (FIG. 1A). Addition of control rhTIMP-1 did not lead to change in the FACS shift, however, GPI-anchored TIMP-1 resulted in a strong surface signal for TIMP-1.

To demonstrate that the exogenously added protein was GPI anchored, RCC-53 cells were first incubated with TIMP-1-GPI protein (200 or 700 ng/ml), and then treated with 60 ng/ml phospholipase C (PLC). FACS analysis demonstrated the complete loss of TIMP-1 cell surface signal following PLC digestion (FIG. 1B). To measure the efficiency of TIMP-1-GPI integration, the TIMP-1 freed from the membrane was collected in the wash buffers, and quantified using TIMP-1 specific ELISA (FIG. 1C). The results show that 66% of the starting TIMP-1 antigen was recovered from the 200 ng/ml sample, while 31% could be recovered from the 700 ng/ml incubation.

Example 2

TIMP-1-GPI Protein Blocks Release of proMMP-2 and proMMP-9 from RCC-53

An increased expression of MMP-2 and MMP-9 correlates with a poor prognosis of RCC (Hemmerlein et al., 2004). The stage IV clear cell carcinoma cell line RCC-53 constitutively secretes both proMMP-2 and proMMP-9 (FIG. 2). The effect of increasing surface TIMP-1 levels on the constitutive release of MMP-2 and MMP-9 proteins was tested using gelatinase zymography assays (Djafarzadeh et al., 2004; Klier et al., 2001). rhTIMP-1 protein at 600 or 1200 ng/ml had no effect on proMMP-2 or proMMP-9 secretion. In contrast, starting at 10 ng/ml, TIMP-1-GPI treatment showed a concentration-dependent decrease of both proMMP-2 and proMMP-9 release into the growth media.

Example 3

Treatment with TIMP-1-GPI Leads to Increase in Surface Expression of matrix Metalloproteinases Based on the results of the gelatinase zymography experiments, it is possible that TIMP-1-GPI may act to sequester MMPs on the cell surface. TIMP-1 binds most active forms of MMPs, the exceptions being MMP-14 and MMP-16 (Brew et al., 2000; Lang et al., 2004). Following incubation of RCC-53 with 700 ng/ml of TIMP-1-GPI protein for 24 h, FACS analyses using MMP-1, MMP-2, MMP-3, MMP-7, MMP-8, MMP-9, MMP-12, MMP-13, MMP-14, MMP-15 and MMP-16 specific antibodies showed, with the exception of MMP-14, an increase in mean channel fluorescence intensity (MFI) for each of the MMPs. rhTIMP-1 control protein had no obvious effect on the FACS signal (data not shown). The surface expression of other proteins including MHC class I (pan class I and HLA-A2) and ICAM-1 was not effected by TIMP-1-GPI treatment. Digestion of the TIMP-1-GPI treated RCC53 with PLC after one hour (as performed in FIG. 1) showed no increase in MMPs (FIGS. 3A and 3B). The accumulation of MMPs on the cell surface mirrored the reduction in secretion of proMMP-2 and proMMP-9 shown in FIG. 2. To further test this apparent blockade of MMP release, Western blot experiments were performed using monoclonal antibodies directed against MMP-1, MMP-3, MMP-7, MMP-8, MMP-12 and MMP-13 on media (serum free) derived from control RCC53 cells or cells treated 24 hours with 700 ng/ml of either rhTIMP-1 or TIMP-1-GPI (FIG. 3C). The presence of each of the MMPs was detected in the media from control RCC-53 cells. Incubation with rhTIMP-1 did not eliminate secretion of the MMPs. In contrast, TIMP-1-GPI appeared to completely block the release of each MMP studied.

To assess the effect of this surface accumulation of MMPs on the ability of the cells to invade ECM, the migration/invasion capacity of the cells was tested using a modified Boyden chamber assay with ECM coated membranes. The overall ability of the RCC-53 cells to invade ECM was not very pronounced (data not shown). To enhance invasion, increasing levels of vascular endothelial growth factor (VEGF) were applied to the lower wells and the experiments were run for 48 hrs. An optimal invasion response was seen at 4 ng/ml VEGF (data not shown) and this response was set as baseline invasion, or zero % inhibition (FIG. 3D). RCC-53 cells pre-treated for 30 minutes with 350 or 700 ng/ml of either rhTIMP-1, or TIMP-1-GPI were then washed, and applied to the top well of the Boyden chamber. The relative increase or decrease in migration/invasion was then determined (see Materials and Methods). While treatment with rhTIMP-1 partially blocked invasion of the cells, TIMP-GPI at 700 ng/ml completely blocked invasion of the RCC-53 cells (FIG. 3D).

Example 4

GPI-Anchored TIMP-1 Effects Proliferation of RCC

To assess the effect of TIMP-1 surface engineering on the proliferation of RCC, MTT assays were performed. The exogenously added TIMP-1-GPI protein was found to elicit a dose-dependent decrease in proliferation of RCC-53 and A498 at 24, 48 and 72 hours (FIG. 4B). RCC-26 cells proliferate extremely slowly (48+ h doubling rate) and the general trend suggested a suppression of proliferation (FIG. 4C). Additional controls using phosphatidylinositol at an equal molar concentration to the TIMP-1-GPI reagent (Sigma, Germany, Nr. P6636) did not lead to significant changes in proliferation of the cells (data not shown).

Example 5

Cell-Mediated Cytotoxicity

MMP activity has been linked to the sensitivity of target cells to apoptosis induced by cytotoxic T cell activity (both perforin/granzyme and FAS-mediated apoptosis) (Egeblad & Werb, 2002). The effect of TIMP-1-GPI on cell-dependent killing of RCC was tested using allogeneic CTL- and NK cell-induced apoptosis. In the allogeneic CTL mediated assays, RCC-53, A498 and RCC-26 target cells were treated with 700 ng/ml of rhTIMP-1 or TIMP-1-GPI, then labeled with $Cr^{51}$ and incubated with allogeneic CD8+ CTL JB4 (FIG. 5A) or NK cell lines (FIG. 5B). The RCC tumor cell lines were recognized and effectively killed by both the CTL and NK cells. Treatment with TIMP-1 or TIMP-1-GPI did not alter the susceptibility of the three RCC lines to either CTL or NK cell mediated apoptosis.

Example 6

TIMP-GPI Treatment Renders RCC Sensitive to FAS-Mediated Killing

The CTL/NK-experiments showed that TIMP-1-GPI treatment did not influence the perforin/granzyme-mediated lytic pathway measured in the chromium-release assay. This pathway acts quickly using the secretion of stored cytotoxins to initiate apoptosis and represents one of the two major immune-initiated cell death mechanisms (Trapani et al., 2000). The second pathway involves FAS/CD95-ligation. The effect of TIMP-1-GPI treatment on FAS-mediated apoptosis was then determined.

FAS expression on the RCC lines was first assessed by flow cytometry using a non-activating anti-FAS mAB (L-958) (H. Engelmann, unpublished results). Untreated cells and cells treated with 700 ng/ml TIMP-1-GPI or rhTIMP-1 control protein for 24 h were stained with L-958 and analyzed. FAS-protein was strongly expressed by all three RCC lines. Treatment with TIMP-1-GPI or rhTIMP-1 did not affect cell surface expression of FAS (FIG. 6A).

The anti-FAS mAB L-957 can induce apoptosis in FAS-expressing cells (H. Englemann, unpublished results). The binding of annexin V-fluoroisothiocyanate (FITC) and incorporation of propidium iodide (PI) into RCC cells after treatment with L-957 was used to detect apoptosis by flow cytometry. As demonstrated in FIG. 6B, RCC-26 and RCC-53 were largely resistant to FAS-mediated apoptosis. The fluorescence intensity (MFI) of untreated and L-957-treated cells was similar. A slight increase in MFI was seen in the RCC-53 in response to L-957 treatment. These observations are in line with previous reports that RCC is generally resistant to FAS-mediated apoptosis (Frost et al., 2003). Treatment with TIMP-1-GPI (L-957+TIMP-1-GPI), but not control rhTIMP-1 (L-957+rhTIMP-1), rendered the cell lines sensitive to FAS-mediated apoptosis (FIG. 6B). A498 was found to be more sensitive to the activating anti-FAS mAB (detected by increased annexin-MFI in L-957-treated samples), TIMP-1-GPI treatment, but not rhTIMP-1, significantly enhanced apoptosis of the A498 cells.

While the RCC-26 and A498 cells showed a dramatic increase in FAS induced apoptosis following TIMP-1-GPI treatment, the RCC-53 cell line showed a less pronounced increase in sensitivity (change in MFI from 62 to 93). To confirm the TIMP-1-GPI/FAS-induced apoptosis of RCC-53, a second ELISA assay based on detection of cytoplasmic chromatin was employed. Advantages of this assay include the lack of subjectivity in interpreting the results and its increased sensitivity relative to the annexin V stain. The chromatin ELISA is able to detect as few as 300 apoptotic cells and measures apoptosis events considerably downstream from the early presence of annexin V on the cell surface. As was found in the annexin V FACS analysis (FIG. 6B), treatment of RCC-53 with L-957 alone induced a slight increase in apoptosis (FIG. 6C). However, treatment of RCC-53 cells with TIMP-1-GPI dramatically increased sensitivity of the cells to anti-FAS-induced apoptosis in a dose-dependent manner.

The results demonstrate that treatment of cancer cells with GPI-anchored TIMP effects killing of the cancer cells by FAS-induced apoptosis. Therefore, GPI-anchored TIMP is useful as anti-tumor agent.

Example 7

TIMP-1-GPI Treatment of RCC Reduces BCL-2 and Increases BAX Protein Expression

The BCL-2 proteins represent a family of proteins involved in the control of apoptosis (reviewed in Igney & Krammer, 2002). Some members of this family (such as BCL-2 and BCL-XL) are anti-apoptotic, while others (such as Bad or BAX) are pro-apoptotic. The sensitivity of cells to apoptotic stimuli can depend on the balance between pro- and anti-apoptotic BCL-2 family members (Igney & Krammer, 2002). The effect of TIMP-1-GPI treatment on the expression of BCL-2 and BAX was then determined. After a 24 h preincubation with 700 ng/ml of TIMP-1-GPI or rhTIMP-1 control, RCC cells were stimulated with 1 lig/ml L-957 (or control mAB) for an additional 16 h. The level of BCL-2 and BAX protein was then determined using intracellular FACS and Western blot. In all three cell lines, treatment with TIMP-1-GPI increased expression of pro-apoptotic BAX, and decreased expression of anti-apoptotic BCL-2. A similar pattern was seen in Western blot assays (FIGS. 7A, B and C).

Example 8

Incorporation of Exogenously Added TIMP-1-Mucin-GPI into the Surface of RCC-53

TIMP1-mucin-GPI protein was generated, and isolated as described in example 1. The incorporation of purified GPI-TIMP-1 protein into the surface membranes of RCC-53, RCC-26 or A498 RCC cell lines was demonstrated by incubation of the cell lines with 700 ng/ml of purified TIMP-1-mucin-GPI or recombinant human (rh)TIMP-1 control protein for one hr. Surface associated TIMP-1-mucin-GPI protein was then detected using FACS. The TIMP-1-mucin-GPI construct was efficiently incorporated into the surface membrane and effectively promotes anti-tumor activity.

Example 9

TIMP-GPI for the Treatment of Residual Cancer in an Individual

The TIMP-1-GPI or TIMP-mucin-GPI reagent is applied at 1 μg/ml locally into the resection area after surgical tumor excision. An inoperable tumor, glioblastoma (astrocytoma grad IV WHO) is surgically removed and the reagents are installed before wound closure.

Example 10

TIMP-GPI for the Treatment of Residual Cancer in an Individual

An amount of at 1 μg/ml of TIMP-1-GPI or TIMP-mucin-GPI reagent is applied locally into the resection area after surgical tumor excision. A tumor, breast cancer at advanced stage, is surgically removed and the reagents are installed before wound closure, particular if there is a clinical risk of local relapse.

Example 11

Evaluation of TIMP-GPI in Models of Tumor Metastasis

The effect of TIMP-1-GPI on tumor metastasis was evaluated. Using a murine model, a T cell lymphoma that efficiently metastasizes to the liver was pretreated with either TIMP-1-GPI or rhTIMP-1-control protein. The resulting tumor was then administered via the tail vein, and the distribution of the tumor in the liver was determined three and seven days later. The results demonstrate that TIMP-1-GPI treated cells show a significantly reduced level of micrometastasis relative to the TIMP-treated control cells.

Example 12

Matrigel Invasion Assays

The effect of TIMP-1-GPI on the tumor cell lines of Example 11 was assayed in a series of Matrigel experiments. The results confirmed that TIMP-1-GPI had a profound effect on the ability of the T cell tumor line cells to undergo Matrigel invasion in relation to rhTIMP-1.

Example 13

Effect of TIMP Fusion Constructs on Fibronectin Production of Fibroblasts

Confluent fibroblasts were cultured in the presence or absence of rhTIMP-1 and TIMP-1-GPI. Expressed and secreted fibronectin was quantified by Western blot analysis using anti fibronectin antibodies (β-actin served as a control). FIG. 9 depicts the results of this experiment and clearly demonstrates that rhTIMP-1 (at 700 ng/ml) did not lead to any significant decrease in fibronectin expression, while TIMP-1-GPI (at 700 ng/ml) strongly reduced the fibronectin that was secreted by the fibroblasts.

Additionally, fibronectin RNA transcribed by fibroblasts was assessed by Northern blot analysis. Fibroblasts were cultured in the presence (FIG. 10A) or absence (FIG. 10B) of 10 ng/ml of the fibroblast activating TNF-α together with 350 ng/ml TIMP-1-GPI or 700 ng/ml TIMP-1-GPI, denatured TIMP-1-GPI and rhTIMP-1-GPI, respectively. Furthermore, either 0%, 1%, 5% o 10% FCS were present in the culturing medium.

These results clearly demonstrate that at a concentration of 350 ng/ml of TIMP-1-GPI, the transcribed fibronectin RNA was significantly reduced, independently of whether TNF-α was present in the medium or not, and independently of the FCS content of the medium. At 700 ng/ml of TIMP-1-GPI, fibronectin RNA was barely detectable.

Thus, the TIMP-GPI fusion construct efficiently inhibits both the synthesis and secretion of the growth factor fibronectin in fibroblasts.

Example 14

Effect of TIMP Fusion Constructs on IL-6 Production of Fibroblasts

The Northern blot analysis of Example 13 was repeated using a probe for IL-6 RNA. Thus, fibroblasts were cultured in the presence (FIG. 11A) or absence (FIG. 11B) of 10 ng/ml of the fibroblast activating TNF-α together with 350 ng/ml TIMP-1-GPI or 700 ng/ml TIMP-1-GPI, denatured TIMP-1-GPI and rhTIMP-1-GPI, respectively. Furthermore, either 0%, 1%, 5% o 10% FCS were present in the culturing medium (FIG. 11).

The results clearly demonstrate that already at a concentration of 350 ng/ml of TIMP-1-GPI, the transcribed IL-6 RNA was strikingly reduced—independently of whether TNF-α was present in the medium, and independently of the FCS content of the medium.

Thus, the TIMP-GPI fusion construct efficiently inhibits the synthesis and secretion of yet another important cytokine involved in wound healing, namely IL-6, in fibroblasts.

Example 15

Effect of TIMP Fusion Constructs on Collagen Production by Fibroblasts

The Northern blot analysis performed in Examples 13 and 14 was repeated using probes for Collagen 1A1 (FIGS. 12A and B), Collagen 4A2 (FIGS. 12C and D), and Collagen 16A1 (FIGS. 12E and F), respectively. Thus, fibroblasts were cultured in the presence (FIGS. 12A, C, E) or absence (FIGS. 12B, D, F) of 10 ng/ml of the fibroblast activating TNF-α together with 350 ng/ml TIMP-1-GPI or 700 ng/ml TIMP-1-GPI, denatured TIMP-1-GPI and rhTIMP-1-GPI, respectively. Furthermore, either 0%, 1%, 5% o 10% FCS were present in the culturing medium.

The results clearly demonstrate that already at a concentration of 350 ng/ml of TIMP-1-GPI, all three transcribed collagen RNAs were significantly reduced, independently of whether TNF-α was present in the medium, and independently of the FCS content of the medium.

Thus, the TIMP-GPI fusion construct efficiently inhibits the synthesis and secretion of collagen, which is one essential protein in ECM production and tissue remodeling.

Example 16

Effect of TIMP Fusion Constructs on TGF-β Production by Fibroblasts

The Northern blot analysis of Examples 13-15 were repeated using probes for TGF-β. Thus, fibroblasts were cultured in the presence (FIG. 13A) or absence (FIG. 13B) of 10 ng/ml of the fibroblast activating TNF-α together with 350 ng/ml TIMP-1-GPI or 700 ng/ml TIMP-1-GPI, denatured TIMP-1-GPI and rhTIMP-1-GPI, respectively. Furthermore, either 0%, 1%, 5% o 10% FCS were present in the culturing medium.

The results clearly demonstrate that already at a concentration of 350 ng/ml of TIMP-1-GPI, almost no TGF-β RNA could be detected—independently of whether TNF-α was present in the medium or not, and independently of the FCS content of the medium.

Therefore, as illustrated by the above Example, the TIMP-GPI fusion construct efficiently inhibits the synthesis and secretion of yet another important cytokine involved in wound healing, namely TGF-β, in fibroblasts.

Example 17

Generation of Further TIMP Fusion Constructs

Further TIMP fusion constructs were generated and purified according to the "Materials and Methods" section, provided below. Specifically, a truncated TIMP-1-GPI fusion construct (SEQ ID NO:1), a truncated TIMP-1-muc-GPI fusion construct (SEQ ID NO:2), a TIMP-2-GPI construct (SEQ ID NO:3), a TIMP-3-GPI construct and a mutated form of the TIMP-3-GPI (SEQ ID NO:4), and a truncated TIMP-1-fractalkine-GPI fusion construct (SEQ ID NO:5) were constructed, expressed and purified.

The truncated TIMP-1-GPI fusion construct (SEQ ID NO: 1) comprises the first 152 amino acids of the human TIMP-1 protein (i.e. the C-terminal amino acids 126-207 were deleted) fused to a GPI-anchor of 36 amino acids in length. The truncated TIMP-1-muc-GPI fusion construct (SEQ ID NO: 2) contains the first 152 amino acids of the human TIMP-1 protein fused to amino acids 256-380 of the human CXCR16 (mucin) further fused to a GPI-anchor of 36 amino acids in length. The resulting fusion construct contains 295 amino acids and has a molecular weight of 32,111 kDa.

By analogy to the full-length TIMP-1-GPI, the TIMP-2-GPI (SEQ ID NO.:3) and TIMP-3-GPI consist of the human TIMP-2 and TIMP-3 protein, respectively, fused to a GPI-anchor 36 amino acids in length. To produce the mutated form of the TIMP-3-GPI fusion construct (SEQ ID NO:4), the GAG binding domain of the human TIMP-3, thought to be responsible for association of the protein with the cell surface, was mutated by the following six exchanges: R43A, K45A, K49A, K53A, K65A, and K68A. The truncated TIMP-1-fractalkine-GPI fusion construct (SEQ ID NO:5) contains the N-terminal portion of the human TIMP-1 (amino acids 1-152) fused to amino acids 100-342 of the human CX3CL1, further fused to the GPI-anchor of 36 amino acids length.

Detailed Examination of the Truncated TIMP-1-GPI (SEQ ID NO: 1), the truncated TIMP-1-Mucin-GPI (SEQ ID NO: 2) and the Truncated TIMP-1-Fractalkine-GPI (SEQ ID NO: 5) Constructs a) Incorporation of Exogenously Added Truncated TIMP-1-GPI, Truncated TIMP-1-Mucin-GPI and Truncated TIMP-1-Fractalkine-GPI into the Cellular Surface Truncated TIMP-1-GPI, truncated TIMP-1-mucin-GPI and truncated TIMP-1-fractalkine-GPI were generated and isolated according to Djafarzadeh et al., 2004. The incorporation of purified fusion constructs into the cell surface membranes of RCC-53, RCC-26 or A498 RCC cell lines is demonstrated by incubation of the cell lines for one hour with 700 ng/ml of purified truncated TIMP-1-GPI, truncated TIMP-1-mucin-GPI and truncated TIMP-1-fractalkine-GPI, respectively, and compared to that of the respective truncated TIMP-1 control TIMP-1 protein that is lacking the mucin, fractalkine and GPI domains. Surface-associated protein was then detected using FACS analysis. It was expected that the addition of control TIMP-1 would not lead to any change in the FACS shift, however, the truncated TIMP-1-GPI, truncated TIMP-1-mucin-GPI and truncated TIMP-1-fractalkine-GPI, respectively, in fact resulted in a strong surface signal for TIMP-1.

To demonstrate that the exogenously added protein was GPI-anchored, RCC-53 cells were first incubated with truncated TIMP-1-GPI, truncated TIMP-1-mucin-GPI and truncated TIMP-1-fractalkine-GPI, respectively (200 or 700 ng/ml), and then treated with 60 ng/ml phospholipase C (PLC). FACS analysis was expected to show a complete loss of TIMP-1 cell surface signal following PLC digestion. To measure the efficiency of integration of the anchored TIMP constructs, the TIMP-1 constructs freed from the membrane were collected in the wash buffers, and quantified using TIMP-1 specific ELISA. It was expected that the majority of the starting TIMP-1 antigen would be recovered from the 200 ng/ml sample.

b) Truncated TIMP-1-GPI, Truncated TIMP-1-Mucin-GPI, and Truncated TIMP-1-Fractalkine-GPI Proteins Block Release of proMMP-2 and proMMP-9 from RCC-53

An increased expression of MMP-2 and MMP-9 typically correlates with a poor prognosis of RCC (Hemmerlein et al., 2004). The stage IV clear cell carcinoma cell line RCC-53 constitutively secretes both proMMP-2 and proMMP-9 (FIG. 2). The effect of increasing surface TIMP-1 levels on the constitutive release of MMP-2 and MMP-9 proteins was tested using gelatinase zymography assays (Djafarzadeh et al., 2004; Klier et al., 2001). rhTIMP-1 protein at 600 or 1200 ng/ml had no effect on proMMP-2 or proMMP-9 secretion. In contrast, starting at 10 ng/ml, truncated TIMP-1-GPI, truncated TIMP-1-mucin-GPI and truncated TIMP-1-fractalkine-GPI treatment, respectively, were expected to show a concentration-dependent decrease of both proMMP-2 and proMMP-9 release into the growth media, comparable to the TIMP-1-GPI treatment described in Example 2.

c) Truncated TIMP-1-GPI, Truncated TIMP-1-Mucin-GPI, and Truncated TIMP-1-Fractalkine-GPI Proteins Impact the Proliferation of RCC To assess the effect of TIMP-1 surface engineering on the proliferation of RCC, MTT assays were performed. The exogenously added truncated TIMP-1-GPI, truncated TIMP-1-mucin-GPI and truncated TIMP-1-fractalkine-GPI proteins, respectively, were expected to elicit a dose-dependent decrease in proliferation of RCC-53 and A498 at 24, 48 and 72 hours comparable to Example 4. RCC-26 cells were expected to proliferate extremely slowly (48+ h doubling rate); the general trend indeed suggested a suppression of proliferation.

Example 18

Further Evaluation of the Further Fusion Constructs of Example 17

The experiments of Examples 1-16 were repeated using the fusion constructs of Example 17; similar results were expected. In particular, the TIMP-2 fusion constructs inhibited most MMPs (except MMP-9) and preferentially inhibited MMP-2. The TIMP-3 fusion constructs inhibited MMP-1, -2, -3, -9, and 13, as well as TACE. The mutant of the TIMP-3 fusion construct (SEQ ID NO.:4) was examined with respect to its integration properties, which additionally showed an improved ability to integrate into the cell membrane (these experiments were carried out according to the methods provided by Example 8). The truncated TIMP-1 fusion constructs (SEQ ID NOs:1, 2, 5) exhibited similar biological functions compared to the full-length TIMP-1 fusion constructs, thus supporting the notion that the N-terminal portion of the TIMPs is essential for their inhibitory function. The fractalkine fusion construct (SEQ ID NO:5) further showed a membrane integration capacity comparable to that of the mucin fusion construct (SEQ ID NO.:4).

Discussion of the Results

The cell-surface engineering using GPI-anchored proteins according to the present invention offers several advantages over traditional gene transfer approaches. 1) The method is applicable to cells that are difficult to transfect, e.g., FAS-mediated apoptosis resistant RCC cells, but also primary cultures, bone marrow progenitors, and immune system cells. 2) The method can be used when only a small number of cells are available or when cells cannot be easily propagated. 3) The cell surface can be modified irrespective of the cell type. 4) The amount of the protein ultimately displayed on the cell surface can be precisely controlled. 5) Multiple GPI-anchored proteins can be incorporated sequentially or simultaneously into the same cells.

Human RCC is a progressive tumor with limited therapeutic options due to tumor resistance to current chemotherapeutic agents and radiation. Immunotherapies are of benefit for some patients suggesting that RCC can be targeted by immune effector mechanisms. Tumor-infiltrating lymphocytes such as CD8+ CTL or NK cells are often seen in renal cancer tissues and often recognize autologous tumor cells when tested in vitro (reviewed in Schendel et al., 1997). Despite these promising observations, tumors generally continue to grow indicating that RCC might have acquired resistance to cytotoxic mechanisms. For a productive anti-tumor response to occur, the immune system must not only recognize the tumor, but the cancer cells must also be susceptible to the killing mechanisms utilized by CTL or NK cells. Cancer cells have evolved various mechanisms to evade immune defenses including reduced sensitivity to apoptosis (reviewed in Dunn et al., 2004).

CTL and NK cells kill their target cells by perforin/granzyme- or FAS/FASL-dependent apoptosis (Kagi et al., 1994). The relative importance of granule exocytosis versus FAS/FASL mediated lytic activities for tumor control in vivo is controversial. While many studies point to a dominance of the granule exocytosis mechanism other studies using perforin-knock-out mice (Seki et al., 2002) suggest that FAS-dependent apoptosis may constitute a more prominent pathway in vivo. Most tumor cells, including RCC, are intrinsically resistant to FAS-mediated killing (Frost et al., 2003). The use of GPI-anchored TIMP represents a promising therapeutic approach for rendering tumor cells susceptible to FAS-mediated apoptosis.

We have shown in the present invention that the engineering of cells by exogenous addition of GPI-TIMP-1 can elicit enhanced as well as novel TIMP-1 biologic activities. Exogenously administered TIMP-1-GPI becomes efficiently inserted into the cell membranes of RCCs and induced a variety of biological effects in the RCC lines with potential therapeutic relevance.

Furthermore, GPI-anchored TIMP-1 protein dramatically altered the cell surface association of diverse RCC-expressed MMPs. This was mirrored by a reduced secretion of MMPs, including proMMP-2 and proMMP-9, from the RCC cells. While TIMP-1 will block the enzymatic activity of MMP-2, it is not thought to bind to the pro-form of the enzyme. Yet the data demonstrating a blockade of proMMP-2 secretion following TIMP-1-GPI treatment are suggestive of this action. It appears that addition of a GPI anchor to TIMP-1 leads to an altered surface stochiometry has enhanced the capacity of the TIMP-1 protein to bind MMPs.

This apparent increased binding of TIMP-1-GPI was also demonstrated with membrane-type MMPs. While not much is known about TIMP-1 association with MMP-15, binding of TIMP-1-GPI protein to MMP-16 would not be predicted to occur based on the rather poor avidity of native TIMP-1 for this protein (Lang et al., 2004). Mutational analysis of the TIMP-1 loops critical for MMP-16 binding show that small, apparently insignificant changes in TIMP-1 can dramatically shift its inhibitory/binding characteristics. In this instance, the altered stochiometry of TIMP-1 on the cell surface appears to have been sufficient to shift its binding to MMP-16. The sequestering of MMPs on the cell surface was also associated with a reduced capacity of RCC-53 cell line to undergo ECM invasion.

As demonstrated in the present invention, TIMP-1-GPI treatment leads to a pronounced dose-dependent reduction in proliferation of the RCC lines. Perhaps most significantly, the normally FAS-apoptosis resistant RCC lines were rendered sensitive to FAS/CD95-mediated killing following treatment with the TIMP-GPI protein of the invention. However, the agent did not affect sensitivity to the perforin pathway. This suggests that GPI-anchored TIMP mediates its anti-tumor effect by the FAS-induced apoptosis pathway rather than by perforin/granzyme-mediated killing by CTL/NK cells.

The FAS-apoptosis pathway is regulated by caspase activation, while the cellular membrane damage by CTL/NK utilizing granule exocytosis, as measured by the chromium-release assay, occurs independent of caspases (Sayers et al., 1998; Seki et al., 2002; Trapani et al., 2000). Upstream events leading to caspase activation involve the balance between pro- and anti-apoptotic BCL-2-family proteins. As demonstrated in the present invention, GPI-TIMP-1 treatment resulted in a down-regulation of anti-apoptotic BCL-2 protein and a corresponding increase in pro-apoptotic BAX protein. This shift towards a higher concentration of pro-apoptotic proteins may be one reason for the increased sensitivity of FAS-mediated apoptosis of TIMP-1 surface engineered RCC cells. These observations represent a novel action for TIMP-1. Similar actions were also shown for TIMP-3 and other TIMPs (TIMP-2 and TIMP-4) (data not shown).

The overexpression of TIMP-1, -2, or -3 in vascular smooth muscle cells using adenoviral vectors was found to inhibit their migration through model basement membranes. The overexpression of TIMP-1 had no effect on cell proliferation, while TIMP-2 caused a dose-dependent inhibition of cell proliferation. The overexpression of TIMP-3 also caused a dose-dependent inhibition of proliferation and in addition lead to apoptosis through mitochondrial membrane de-polarisation and leakage of cytochrome-c (Baker et al., 1999; Baker et al., 1998; Smith et al., 1997). TIMP-3 is the only TIMP protein that selectively binds to the surface of cells independent of association with other surface proteins (Majid et al., 2002; Smith et al., 1997). Focusing TIMP-1 to cell surfaces via a GPI-anchor leads to novel biologic actions that appear to mimic effects reported for TIMP-3.

TIMP-3 has been shown to sensitize melanoma cells to apoptosis induced by anti-FAS-antibody, TNF-alpha and TRAIL. The mechanism of action was linked to a general stabilization of FAS, TNF-RI and TRAIL-RI on the surface of the TIMP-3 treated melanoma cells (Ahonen et al., 2003). This increased surface expression of the receptors was linked to activation of caspase-8 and caspase-3 (Ahonen et al., 2003).

In the experiments detailed in the present invention, the RCC cells did not show a change in FAS surface expression following treatment with TIMP-1-GPI (FIG. 6A). In addition, the RCC cells remained resistant to TNF-α induced apoptosis (tested from 100 to 10,000 units per ml) irregardless of TIMP-GPI treatment (data not shown). FACS analysis of the RCC cells subsequently showed barely detectable levels of TNF-RI (p55) and TNF-RII (p75) on RCC-53 and no expression on the RCC-26 or A498 lines (data not shown). The surface expression did not change with treatment with TIMP-1-GPI. Thus, the increased sensitivity to FAS mediated apoptosis following treatment with TIMP-1-GPI does not appear to be mediated through a general stabilization of death receptor proteins on the cell surface. What is clear is that treatment with TIMP-1-GPI does alter the balance of Bcl-2 proteins to elicit a more “pro-apoptotic” expression profile.

The results of the present invention provide an additional link between tumor biology, MMP/TIMP function and apoptosis pathways. Linking TIMP proteins to GPI directly or via mucin domains represent a powerful anti-tumor agent to render tumor cells, which are normally resistant against FAS-induced apoptosis, sensitive for FAS-induced apoptosis. By this mechanism tumor cells will be effectively killed.

Regarding the use of the fusion constructs—in particular, the TIMP-1-GPI construct, the TIMP-1-muc-GPI construct and those as set forth in SEQ ID NOs:1, 2, 3, 4 and 5—in the field of regenerative medicine, e.g. wound healing, the TIMP-GPI constructs of the present invention have been herein shown to efficiently inhibit the production and secretion of important enzymes and cytokines (fibronectin, collagen, IL-6, TGF-β) involved in the processes of tissue remodeling and fibrosis which lead to an increased ECM production. Thus, the members of the TIMP family (TIMP-1, TIMP-2, TIMP-3, TIMP-4), if anchored in the cell membrane by means of a GPI-anchor or a mucin or a fractalkine and a GPI, can be used to efficiently modulate the processes of wound healing by influencing the delicate balance between ECM production and ECM turnover.

Materials and Methods

Cell Lines and Cell Culture

The RCC lines, RCC-53 and RCC-26, and were generated by D.J.S. (Munich, Germany) from patient samples. RCC-53, RCC-26 and A498 (American Type Culture Collection) (Giard et al., 1973) were cultured in RPMI1640 medium (GIBCO BRL, Life Technologies GmbH, Eggenstein, Germany) supplemented with 2 mM L-glutamine (Biochrom KG, Berlin), 1 mM sodium pyruvate (GIBCO BRL, Life Technologies GmbH, Eggenstein, Germany), 12% heat-inactivated FCS (Biochrom KG, Berlin, No. S01 15). Fresh medium was given every third day and cultures were split when cells were confluent.

Cytotoxic effector cells: JB4 is a HLA-A2-alloreactive cytotoxic T effector clone generated in our own facility (E.N.) and is expanded by biweekly stimulation as described (Milani et al., 2005). It is used in cytotoxicity assays on day 7 or 8 after stimulation. The human NK leukemic lines, NKL (Robertson et al., 1996) and NK-92 (Gong et al., 1994), were kindly provided by C. S. Falk (GSF-Institute of Molecular Immunology, Munich, Germany) and cultured in medium containing 15% heat-inactivated FCS and 100 U/ml recombinant IL-2. The day before use in cytotoxicity assays, the culture was adjusted to $0.3\times10^6$ cells/ml in fresh medium.

Fluorescence-Activated Cell Sorting (FACS) Analysis

Cells were detached with 1.5 mM EDTA (Biochrom A, Berlin, Germany No. L2113) in 1×PBS and incubated for 60 min on ice with antibodies specific for human; TIMP-1 (IM32L), MMP-1 (IM35L-100), MMP-3 (IM36L-100), MMP-8 (IM38L) (CALBIOCHEM, Merck Darmstadt, Germany); MMP-9 (IM 61-100), MMP-2 (IM 51L) (ONCOGENE, Bad Soden, Germany); MMP-7 (MAB907), MMP-12 (MAB917), MMP-14 (MAB9181) (R&D Systems, Minneapolis, USA); MMP-13 (IM44L), MMP-15 (IM48L), MMP-16 (IM50L) (CALBIOCHEM, Merck Darmstadt, Germany) and $IgG1_{\kappa}$ (SIGMA-ALDRICH, Taufkirchen, Germany No. M9269). ICAM-1 and HLA-antibodies (W6/32 and HB82) were described previously (Johnson et al., 1988; Barnstable et al., 1978; Parham & Brodsky, 1981). Anti-FAS (H. Engelmann, unpublished data), anti-TNF-RI, anti-TNF-RII and isotype control antibodies were used as described (Bigda et al., 1994). Cells were washed three times with 1×PBS, incubated with FTIC-conjugated donkey anti-mouse mAB (DAKO A/S, Glostrup, Denmark No. F0313) for 45 min on ice, then washed three times with 1×PBS and analyzed using a flow cytometer (FACSCalibur, Becton, Dickinson and Company, San Jose, Calif., USA) and CellQuest software. Anti-BCL-2 (ALX-804-225) and anti-BAX (ANC-357-040) antibodies were obtained from ALEXIS (Grunberg, Germany).

Purification of TIMP-1-GPI Protein

The TIMP-1-GPI protein was produced and purified as previously described (Djafarzadeh, et al. 2004). Briefly, human TIMP-1 was cloned from cDNA using hTIMP-1 specific primers, fused without a translation stop codon to the GPI-signal sequence cloned from LFA-3 (Kirby et al., 1995; Medof et al., 1996) and subcloned into pEF-DHFR and stably introduced into DHFR deficient Chinese hamster ovary (CHO) cells and selected as described (Mack et al., 1995). TIMP-1-GPI-fusion protein was purified from the CHO cells by Triton X-100 detergent extraction followed by column purification using DEAE, heparin sepharose and size exclusion (Djafarzadeh et al., 2004).

TIMP-1 ELISA

A human TIMP-1 specific ELISA using the protocol applied according to the manufacture's directions (MAB970, R&D Systems) was used to monitor levels of TIMP-1 in solution. The coating anti-human TIMP-1 mAB (MAB970), biotinylated anti-human TIMP-1 detection mAB (BAF970) and rhTIMP-1 protein (970-TM) were purchased from R&D Systems GmbH (Wiesbaden, Germany).

Incorporation of TIMP-1-GPI into Cell Membranes

RCC-53 cells ($5\text{-}10\times10^6$ cells/nil) were incubated with 200 to 700 ng/ml of purified hTIMP-1-GPI at 37° C./5% CO2. The cells were then washed three times with cold PBS and analyzed by FACS using human TIMP-1 specific monoclonal antibodies (see above).

GPI-Anchor Cleavage by Phospholipase C

Cells ($5\text{-}10\times10^6$ cells/nil) were incubated with 200 or 700 ng of TIMP-1-GPI or rhTIMP-1 protein in serum-free medium for 1 h at 37° C. by 5% CO2. The cells were washed three times with cold PBS and treated with 60 ng/ml phosphatidylinositol-specific phospholipase C (SIGMA-ALDRICH, Taufkirchen, Germany No. 661-9) in serum-free medium for 30 min at 37° C./5% CO2. Cells were washed three times, all supernatants were harvested.

Proliferation

RCC-53, A498 or RCC-26 cells ($30\times10^3$/100 µl medium) were cultured in 96-well micro-titer plates for 24 h under standard conditions to yield firmly attached and stably growing cells. After discarding supernatants, 50|il of medium containing TIMP-1-GPI, buffer, or rhTIMP-1 was added to cells and incubated for 24 to 72 h. Then 50|il of a 1 mg/ml solution of (3,5-Dimethylthiazol-2-yl]-2,5-diphenyl-tetrazolium bromide) MTT (SIGMA-ALDRICH, Taufkirchen, Germany No. M2128) was added. After 3-h incubation at 37° C., formazan crystals were dissolved by addition 100 µl isopropanol and 0.04 N HCl. Absorbance was then measured at 550 nm using GENios plus TEC AN ELISA reader. For each experiment at least 6-wells were analyzed per experimental condition and time point.

Zymography

RCC-53 cells were cultured in 24 well plate ($5\times10^4$ cells/well). The medium was exchanged for 24 h with serum-free medium containing either rhTIMP-1 or increasing amounts of TIMP-1-GPI and incubated for 24 h, 48 h and 72 h. Cell supernatants were analyzed by gelatin zymography using 10% SDS-polyacrylamide gels (Invitrogen, Groningen, Netherlands, No. EC61755BOX) as described (Djafarzadeh et al., 2004). Recombinant MMP-9 enzyme (Amersham Biosciences, Uppsala, Sweden, No. RPN2634) was used as positive control.

Extracellular Invasion Assay

The effect of TIMP-1-GPI vs. rhTIMP-1 treatment on the ability of the cells to invade ECM was evaluated using a commercial cell invasion assay (Chemicon International. Inc., Temecula, Calif., No. ECM 555). RCC-53 cells were first analyzed for their ability to invade ECM. Invaded cells in the bottom of the insert were detached, lysed and detected by CyQuant dye as described in the accompanying protocol. Increasing levels of vascular endothelial growth factor (VEGF) 2 ng/ml to 8 ng/ml was used to enhance invasion. Optimal migration was seen at 4 ng/ml VEGF (data not shown). The effect of treatment with 350 ng/ml and 700 ng/ml of control rhTIMP-1 or TIMP-1-GPI on migration was then determined. To quantify the potential effects of the TIMP agents, baseline migration of the RC-53 cells to 4 ng/ml VEGF was set as 0. The value for 100% "inhibition" to VEGF induced migration was set as the migration/invasion of RCC-53 cells in the absence of VEGF. The resultant effects of rhTIMP or TIMP-1-GPI treatment on RCC-53 invasion was calculated as percent change (negative or positive) relative to the "maximal" value.

Annexin-V-Detection of Apoptosis

Detection and quantification of apoptotic vs. necrotic cells at the single cell level was performed using annexin-V-FLUOS staining Kit (Becton, Dickinson and Company, Heidelberg, Germany, No. 556547). RCC-53 cells were seeded at $1\times10^6$ cells/well into 24-well plates and allowed to attach over night. The wells were then rinsed 3 times with 1×PBS and 1 ml of serum-free RPMI 1640 medium was added, followed by 700 ng/ml of TIMP-1-GPI or rhTIMP-1. Cells were incubated for 24 h at 37° C./5% $CO_2$. After 24 h, 1 |ig/ml anti-FAS activating mAB L-957 (H. Engelmann, unpublished data) or isotype control were added and the cells were further incubated for 16 h at 37° C./5% $CO_2$. The cells were washed with PBS, pelleted and resuspended in staining solution (annexin-V-fluorescein labeling reagent and propidium iodide (PI) in Hepes buffer) for 15 min at room temperature. The cells were then analyzed by flow cytometry. A time-course study showed that annexin-V binding in RCC cells precedes PI reactivity.

Measurement of Apoptosis by Chromatin Specific ELISA

Apoptosis was measured using the Cell Death Detection ELISA Plus kit from Roche (Pensberg, Germany, No. 1774425). RCC-53 cells were seeded into a 96-well dish at a concentration of $4\times10^4$ cells/well and allowed to attach over night. The wells were rinsed 3 times with 1×PBS and 200|il of serum-free RPMI 1640 medium was added to each well, followed by 700 ng/ml of TIMP-1-GPI or rhTIMP-1. The cells were then incubated for 24 h at 37° C./5% $CO_2$. After 24 h-incubation with TIMP-1-GPI or rhTIMP-1, 1 |ig/ml activating anti-FAS mAB L-957 or isotype control mAB were added and incubated for 16 h at 37° C./5% $CO_2$. Then the plate was centrifuged and the supernatant was carefully removed. The cell pellet was placed into 200 ml of lysis buffer provided by the manufacturer for 30 min and centrifuged. Aliquots of the supernatant (20 μl) were used in an ELISA with anti-DNA and anti-histone antibodies to detect the presence of cytoplasmic nucleosomes.

Western Blot

Western blot was used for the detection of MMPs in serum free growth media. The anti-MMP antibodies used are described above (FACS analysis). Recombinant human MMP Western blotting standards were purchased from R&D Systems (Minneapolis, USA) and included; MMP-1 (WBC024), MMP-2 (WBC025), MMP-3 (WBC015), MMP-8 (WBC017), MMP-12 (WBC019) and MMP-13 (WBC020). Western blot was also used for the detection of BCL-2, BAX (see above for mAbs) and β-actin (Acris Hiddenhausen, Germany, No. ab8227). All proteins were detected using a commercial Western blot analysis kit, Chemiluminescent Immuno detection System (Invitrogen, Groningen, Netherlands).

Cell-Mediated Cytotoxicity

Target cells were labeled with $Cr^{51}$ for 1-2 h, washed and co-incubated with effector cells at a constant cell number of 2000 cells per well in 96-V bottom plates. Duplicate measurements of four step titrations of effector cells were used in all experiments. Spontaneous and maximum releases were determined by incubating the target cells alone and by directly counting labeled cells, respectively. After 4 h of incubation at 37° C. in a humidified 5% CO2 atmosphere, supernatants were harvested, transferred to Lumaplate solid scintillation microplates, dried over night and counted on a TopCount microplate scintillation counter (Packard, Meriden, Conn.). For each E:T ratio, the percentage of lysis was calculated as follows: % specific lysis=(experimental cpm−spontaneous cpm/maximal cpm−spontaneous cpm)×100. Spontaneous release of target cells was always <15% of the total maximal release.

REFERENCES

Altschul, S. F., Gish, W., Miller, W., Myers, E. W. & Lipman, D. J. (1990) *J. Mol. Biol.* 215:403-410.

Ahonen, M., Poukkula, M., Baker, A. H., Kashiwagi, M., Nagase, H., Eriksson, J. E. & Kahan, V. M. (2003). *Oncogene,* 22, 2121-34.

Baker, A. H., George, S. J., Zaltsman, A. B., Murphy, G. & Newby, A. C. (1999). *Br J Cancer,* 79, 1347-55.

Baker, A. H., Zaltsman, A. B., George, S. J. & Newby, A. C. (1998). *J Clin Invest,* 101, 1478-87.

Barnstable, C. J., Jones, E. A. & Crumpton, M. J. (1978). *Br Med Bull,* 34, 241-6.

Bigda, J., Beletsky, I., Brakebusch, C., Varfolomeev, Y., Engelmann, H., Hohmann, H. & Wallach, D. (1994). *J Exp Med,* 180, 445-60.

Bloomston, M., Shafii, A., Zervos, E. E. & Rosemurgy, A. S. (2002). *J Surg Res,* 102, 39-44.

Bode, W. & Maskos, K. (2003). *Biol Chem,* 384, 863-72.

Bond, M., Murphy, G., Bennett, M. R., Newby, A. C. & Baker, A. H. (2002). *J Biol Chem,* 277, 13787-95.

Brand, K. (2002). *Curr Gene Ther,* 2, 255-71.

Brew, K., Dinakarpandian, D. & Nagase, H. (2000). *Biochim Biophys Acta,* 1477, 267-83.

Brown, O., Cowen, R. L., Preston, C. M., Castro, M. G. & Lowenstein, P. R. (2000). *Gene Ther,* 7, 1947-53.

Djafarzadeh, R., Mojaat, A., Vicente, A. B., von Luttichau, I. & Nelson, P. J. (2004). *Biol Chem,* 385, 655-63.

Dunn, G. P., Old, L. J. & Schreiber, R. D. (2004). *Annu Rev Immunol,* 22, 329-60.

Egeblad, M. & Werb, Z. (2002). *Nat Rev Cancer,* 2, 161-74.

Frost, P., Caliliw, R., Belldegrun, A. & Bonavida, B. (2003). *Int J Oncol,* 22, 431-7.

Giard, D. J., Aaronson, S. A., Todaro, G. J., Arnstein, P., Kersey, J. H., Dosik, H. & Parks, W. P. (1973). *J Natl Cancerinst,* 51, 1417-23.

Gong, J. H., Maki, G. & Klingemann, H. G. (1994). *Leukemia,* 8, 652-8.

Hemmerlein, B., Johanns, U., Halbfass, J., Bottcher, T., Heuser, M., Radzun, H. J. & Thelen, P. (2004). *Int J Oncol,* 24, 1069-76.

Igney, F. H. & Krammer, P. H. (2002). *Nat Rev Cancer,* 2, 277-88.

Itoh, Y. & Nagase, H. (2002). *Essays Biochem,* 38, 21-36.

Johnson, J. P., Stade, B. G., Hupke, U., Holzmann, B. & Riethmuller, G. (1988). *Immunobiology,* 178, 275-84.

Kagi, D., Vignaux, F., Ledermann, B., Burki, K., Depraetere, V., Nagata, S., Hengartner, H. & Golstein, P. (1994). *Science,* 265, 528-30.

Kirby, A. C., Hill, V., Olsen, I. & Porter, S. R. (1995). *Biochem Biophys Res Commun,* 214, 200-5.

Klier, C. M., Nelson, E. L., Cohen, C. D., Horuk, R., Schlondorff, D. & Nelson, P. J. (2001). *Biol Chem,* 382, 1405-10.

Lang, R., Braun, M., Sounni, N. E., Noel, A., Frankenne, F., Foidart, J. M., Bode, W. & Maskos, K. (2004). *J Mol Biol,* 336, 213-25.

Maskos K. and Bode W. (2003) Mol Biotechnol 25:241-266.

Mack, M., Riethmuller, G. & Kufer, P. (1995). *Proc Natl Acad Sci USA,* 92, 7021-5.

Majid, M. A., Smith, V. A., Easty, D. L., Baker, A. H. & Newby, A. C. (2002). *Br J Ophthalmol,* 86, 97-101.

Marinello F., Gazzanelli, G. (2001), Apoptosis, 6(6):479-82.

Medof, M. E., Nagarajan, S. & Tykocinski, M. L. (1996). *FASeb J,* 10, 574-86.

Milani, V., Frankenberger, B., Heinz, O., Brandi, A., Ruhland, S., Issels, R. D. & Noessner, E. (2005). *Int Immunol.*

Moniaux N., Adrianifahanana M., Brand R. E., Batra S. K. (2004), British Journal of Cancer, 91, 1633-1638

Nagase, H. & Woessner, J. F., Jr. (1999). *J Biol Chem,* 274, 21491-4.

Nagata, S. (1999). *Annu Rev Genet,* 33, 29-55. Parham, P. & Brodsky, F. M. (1981). *Hum Immunol,* 3, 277-99. Rigg, A. S. & Lemoine, N. R. (2001). *Cancer Gene Ther,* 8, 869-78.

Pearson W R & Lipman D J. (1988). Proc Natl Acad Sci USA 85:2444-2448

Robertson, M. J., Cochran, K. J., Cameron, C., Le, J. M., Tantravahi, R. & Ritz, J. (1996). *Exp Hematol,* 24, 406-15.

Sayers, T. J., Brooks, A. D., Lee, J. K., Fenton, R. G., Komschlies, K. L., Wigginton, J. M., Winkler-Pickett, R. & Wiltrout, R. H. (1998). *J Immunol,* 161, 3957-65.

Schendel, D. J., Frankenberger, B., Jantzer, P., Cayeux, S., Noessner, E., Willimsky, G., Maget, B., Pohla, H. & Blankenstein, T. (2000). *Gene Ther,* 7, 2007-14.

Schendel, D. J., Gansbacher, B., Oberneder, R., Kriegmair, M., Hofstetter, A., Riethmuller, G. & Segurado, O. G. (1993). *J Immunol,* 151, 4209-20.

Schendel, D. J., Oberneder, R., Falk, C. S., Jantzer, P., Kressenstein, S., Maget, B., Hofstetter, A., Riethmuller, G. & Noessner, E. (1997). *J Mol Med,* 75, 400-13.

Seki, N., Brooks, A. D., Carter, C. R., Back, T. C., Parsoneault, E. M., Smyth, M. J., Wiltrout, R. H. & Sayers, T. J. (2002). *J Immunol,* 168, 3484-92.

Singer A. and Clark R. (1999). N. Engl. J. Med., 341, 738-746.

Smith, M. R., Kung, H., Durum, S. K., Colburn, N. H. & Sun, Y. (1997). *Cytokine,* 9, 770-80.

Span, P. N., Lindberg, R. L., Manders, P., Tjan-Heijnen, V. C., Heuvel, J. J., Beex, L. V. & Sweep, C. G. (2004). *J Pathol,* 202, 395-402.

Trapani, J. A., Davis, J., Sutton, V. R. & Smyth, M. J. (2000). *Curr Opin Immunol,* 12, 323-9.

Vogelzang, N. J. & Stadler, W. M. (1998). *Lancet,* 352, 1691-6.

Zacchigna, S., Zentilin, L., Morini, M., Dell'Eva, R., Noonan, D. M., Albini, A. & Giacca, M. (2004). *Cancer Gene Ther,* 11, 73-80.

The invention claimed is:

1. A method of treating a skin lesion to prevent or inhibit the formation of a scar, the method comprising administering to a site of a skin lesion or scar caused by surgery, burn, injection, bite, vaccination, trauma, or infection a pharmaceutical composition comprising a fusion construct comprising an amino acid sequence of a tissue inhibitor of metalloproteinases (TIMP) or a functionally active portion thereof which retains the activity of TIMP, wherein the functionally active portion comprises a TIMP molecule truncated to the first 50 to 152 N-terminal amino acid residues, and wherein said TIMP or functionally active portion thereof is linked to a glycosylphosphatidylinositol (GPI)-anchor.

2. The method according to claim 1, wherein the scar is a hypertrophic scar or a keloid formation.

3. The method according to claim 1 or 2, wherein the pharmaceutical composition is used together with a detergent, sealant or wilier substance.

4. A method for treating a skin lesion in a subject in need thereof, comprising administering to a site of a skin lesion or scar caused by surgery, burn, injection, bite, vaccination, trauma, or infection in said subject a pharmaceutical composition comprising a fusion construct comprising an amino acid sequence of a tissue inhibitor of metalloproteinases (TIMP) or a functionally active portion thereof which retains the activity of TIMP, wherein the functionally active portion comprises a TIMP molecule truncated to the first 50 to 152 N-terminal amino acid residues, and wherein said TIMP or functionally active portion thereof is linked to a glycosylphosphatidylinositol (GPI)-anchor.

5. The hod according to claim 4, wherein the scar is a hypertrophic scar or a keloid formation.

6. The method according to claim 4 or 5, wherein the pharmaceutical composition is used together with a detergent, sealant or carrier substance.

7. A method of treating a wound in a subject in need thereof, the method comprising administering to a wound of said subject a pharmaceutical composition comprising a fusion construct comprising an amino acid sequence of a tissue inhibitor of metalloproteinases (TIMP) or a functionally active portion thereof which retains the activity of TIMP, wherein the functionally active portion comprises a TIMP molecule truncated to the first 50 to 152 N-terminal amino acid residues, and wherein said TIMP or functionally active portion thereof is linked to a glycosylphosphatidylinositol (GPI)-anchor.

8. The method of claim 7, wherein said wound is a chronic wound.

9. The method of claim 7, wherein said fusion construct is administered at a concentration of 0.5 μg/ml to 5 μg/ml.

10. The method of claim 7, wherein said TIMP is human TIMP-1.

11. The method of claim 10, wherein said pharmaceutical composition further comprises TIMP-2.

12. The method of claim 10, wherein said pharmaceutical composition further comprises TIMP-4.

13. The method of claim 1, wherein said fusion construct is administered at a concentration of 0.5 μg/ml to 5 μg/ml.

14. The method of claim 1, wherein said TIMP is human TIMP-1.

15. The method of claim 14, wherein said pharmaceutical composition further comprises TIMP-2.

16. The method of claim 14, wherein said pharmaceutical composition further comprises TIMP-4.

17. The method of claim 4, wherein said fusion construct is administered at a concentration of 0.5 μg/ml to 5 μg/ml.

18. The method of claim 4, wherein said TIMP is human TIMP-1.

19. The method of claim 18, wherein said pharmaceutical composition further comprises TIMP-2.

20. The method of claim 18, wherein said pharmaceutical composition further comprises TIMP-4.

21. The method of claim 1, wherein said fusion construct is encoded by SEQ ID NO: 1.

* * * * *

SEQUENCE LISTING

```
<160> NUMBER OF SEQ ID NOS: 5

<210> SEQ ID NO 1
<211> LENGTH: 582
<212> TYPE: DNA
<213> ORGANISM: Artificial Sequence
<220> FEATURE:
<223> OTHER INFORMATION: Description of Artificial Sequence: Synthetic
      truncated human TIMP-1 fused to GPI polynucleotide
      sequence

<400> SEQUENCE: 1

gaattcatgg ccccctttga gcccctggct tctggcatcc tgttgttgct gtggctgata     60

gcccccagca gggcctgcac ctgtgtccca ccccacccac agacggcctt ctgcaattcc    120

gacctcgtca tcagggccaa gttcgtgggg acaccagaag tcaaccagac caccttatac    180

cagcgttatg agatcaagat gaccaagatg tataaagggt tccaagcctt aggggatgcc    240

gctgacatcc ggttcgtcta cacccccgcc atggagagtg tctgcggata cttccacagg    300

tcccacaacc gcagcgagga gtttctcatt gctggaaaac tgcaggatgg actcttgcac    360

atcactacct gcagttttgt ggctccctgg aacagcctga gcttagctca gcgccggggc    420

ttcaccaaga cctacactgt tggctgtgag gaatgcacag tgtctagaac aacctgtatc    480

ccaagcagcg gtcattcaag acacagatat gcacttatac ccataccatt agcagtaatt    540
```

```
acaacatgta ttgtgctgta tatgaatgta ttatgagtcg ac                       582
```

<210> SEQ ID NO 2
<211> LENGTH: 900
<212> TYPE: DNA
<213> ORGANISM: Artificial Sequence
<220> FEATURE:
<223> OTHER INFORMATION: Description of Artificial Sequence: Synthetic truncated human TIMP-1 fused to mucin domain and GPI polynucleotide sequence

<400> SEQUENCE: 2

```
gaattcatgg ccccctttga gcccctggct tctggcatcc tgttgttgct gtggctgata      60

gcccccagca gggcctgcac ctgtgtccca ccccacccac agacggcctt ctgcaattcc     120

gacctcgtca tcagggccaa gttcgtgggg acaccagaag tcaaccagac caccttatac     180

cagcgttatg agatcaagat gaccaagatg tataaagggt tccaagcctt aggggatgcc     240

gctgacatcc ggttcgtcta cacccccgcc atggagagtg tctgcggata cttccacagg     300

tcccacaacc gcagcgagga gtttctcatt gctggaaaac tgcaggatgg actcttgcac     360

atcactacct gcagttttgt ggctccctgg aacagcctga gcttagctca gcgccggggc     420

ttcaccaaga cctacactgt tggctgtgag gaatgcacag tgtctagact tgatctcaaa     480

gaatgtggac atgcttactc ggggattgtg gcccaccaga agcatttact tcctaccagc     540

cccccaactt ctcaggcctc agagggggca tcttcagata tccacacccc tgcccagatg     600

ctcctgtcca ccttgcagtc cactcagcgc cccaccctcc cagtaggatc actgtcctcg     660

gacaaagagc tcactcgtcc caatgaaacc accattcaca ctgcgggcca cagtctggca     720

gttgggcctg aggctgggga gaaccagaag cagccggaaa aaaatgctgg tcccacagcc     780

tctagcacaa cctgtatccc aagcagcggt cattcaagac acagatatgc acttataccc     840

ataccattag cagtaattac aacatgtatt gtgctgtata tgaatgtatt atgagtcgac     900
```

<210> SEQ ID NO 3
<211> LENGTH: 599
<212> TYPE: DNA
<213> ORGANISM: Artificial Sequence
<220> FEATURE:
<223> OTHER INFORMATION: Description of Artificial Sequence: Synthetic human TIMP-2 fused to GPI polynucleotide sequence

<400> SEQUENCE: 3

```
gaattcatgg caaccctaga gaggatccag tatgagatca agcagataaa gatgttcaaa      60

gggcctgaga aggatataga gtttatctac acggccccct cctcggcagt gtgtggggtc     120

tcgctggacg ttggaggaaa gaaggaatat ctcattgcag gaaaggccga gggggacggc     180

aagatgcaca tcaccctctg tgacttcatc gtgccctggg acaccctgag caccacccag     240

aagaagagcc tgaaccacag gtaccagatg ggctgcgagt gcaagatcac gcgctgcccc     300

atgatcccgt gctacatctc ctccccggac gagtgcctct ggatggactg ggtcacagag     360

aagaacatca acgggcacca ggccaagttc ttcgcctgca tcaagagaag tgacggctcc     420

tgtgcgtggt accgcggcgc ggcgcccccc aagcaggagt ttctcgacat cgaggaccca     480

tctagaacaa cctgtatccc aagcagcggt cattcaagac acagatatgc acttataccc     540

ataccattag cagtaattac aacatgtatt gtgctgtata tgaatgtatt atagtcgac      599
```

<210> SEQ ID NO 4
<211> LENGTH: 758

<212> TYPE: DNA
<213> ORGANISM: Artificial Sequence
<220> FEATURE:
<223> OTHER INFORMATION: Description of Artificial Sequence: Synthetic mutated human TIMP-3 fused to GPI polynucleotide sequence

<400> SEQUENCE: 4

```
gaattcatga ccccttggct cgggctcatc gtgctcctgg gcagctggag cctgggggac     60

tggggcgccg aggcgtgcac atgctcgccc agccaccccc aggacgcctt ctgcaactcc    120

gacatcgtga tcgcggccgc ggtggtgggg gcgaagctgg tagcggaggg gcccttcggc    180

acgctggtct acaccatcgc gcagatggcg atgtaccgag gcttcaccaa gatgccccat    240

gtgcagtaca tccatacgga agcttccgag agtctctgtg gccttaagct ggaggtcaac    300

aagtaccagt acctgctgac aggtcgcgtc tatgatggca agatgtacac ggggctgtgc    360

aacttcgtgg agaggtggga ccagctcacc ctctcccagc gcaaggggct gaactatcgg    420

tatcacctgg gttgtaactg caagatcaag tcctgctact acctgccttg ctttgtgact    480

tccaagaacg agtgtctctg gaccgacatg ctctccaatt tcggttaccc tggctaccag    540

tccaaacact acgcctgcat ccggcagaag ggcggctact gcagctggta ccgaggatgg    600

gcccccccgg ataaaagcat catcaatgcc acagacccct ctagaacaac ctgtatccca    660

agcagcggtc attcaagaca cagatatgca cttataccca taccattagc agtaattaca    720

acatgtattg tgctgtatat gaatgtatta tagtcgac                            758
```

<210> SEQ ID NO 5
<211> LENGTH: 1314
<212> TYPE: DNA
<213> ORGANISM: Artificial Sequence
<220> FEATURE:
<223> OTHER INFORMATION: Description of Artificial Sequence: Synthetic truncated human TIMP-1 fused to fractalkine domain and GPI polynucleotide sequence

<400> SEQUENCE: 5

```
gaattcatgg ccccctttga gcccctggct tctggcatcc tgttgttgct gtggctgata     60

gcccccagca gggcctgcac ctgtgtccca ccccacccac agacggcctt ctgcaattcc    120

gacctcgtca tcagggccaa gttcgtgggg acaccagaag tcaaccagac caccttatac    180

cagcgttatg agatcaagat gaccaagatg tataaagggt tccaagcctt aggggatgcc    240

gctgacatcc ggttcgtcta cacccccgcc atggagagtg tctgcggata cttccacagg    300

tcccacaacc gcagcgagga gtttctcatt gctggaaaac tgcaggatgg actcttgcac    360

atcactacct gcagttttgt ggctccctgg aacagcctga gcttagctca gcgccggggc    420

ttcaccaaga cctacactgt tggctgtgag gaatccacag tgtctagagg cggcaccttc    480

gagaagcaga tcggcgaggt gaagcccagg accacccctg ccgccggggg aatggacgag    540

tctgtggtcc tggagcccga agccacaggc gaaagcagta gcctggagcc gactccttct    600

tcccaggaag cacagagggc cctggggacc tccccagagc tgccgacggg cgtgactggt    660

tcctcaggga ccaggctccc cccgacgcca aaggctcagg atggagggcc tgtgggcacg    720

gagcttttcc gagtgcctcc cgtctccact gccgccacgt ggcagagttc tgctccccac    780

caacctgggc ccagcctctg ggctgaggca aagacctctg aggccccgtc cacccaggac    840

ccctccaccc aggcctccac tgcgtcctcc ccagccccag aggagaatgc tccgtctgaa    900

ggccagcgtg tgtggggtca gggacagagc cccaggccag agaactctct ggagcgggag    960
```

-continued

```
gagatgggtc ccgtgccagc gcacacggat gccttccagg actgggggcc tggcagcatg   1020

gcccacgtct ctgtggtccc tgtctcctca gaagggaccc ccagcaggga gccagtggct   1080

tcaggcagct ggacccctaa ggctgaggaa cccatccatg ccaccatgga cccccagagg   1140

ctgggcgtcc ttatcactcc tgtccctgac gcccaggctg ccacccggag gcaggctaga   1200

acaacctgta tcccaagcag cggtcattca agacacagat atgcacttat acccatacca   1260

ttagcagtaa ttacaacatg tattgtgctg tatatgaatg tattatgagt cgac         1314
```